US010570131B2

(12) United States Patent
Brias et al.

(10) Patent No.: US 10,570,131 B2
(45) Date of Patent: Feb. 25, 2020

(54) HETEROCYCLIC COMPOUNDS AND THEIR USE IN PREVENTING OR TREATING BACTERIAL INFECTIONS

(71) Applicant: MUTABILIS, Paris (FR)

(72) Inventors: Julie Brias, Paris (FR); Audrey Caravano, Paris (FR); Sophie Chasset, Paris (FR); Francis Chevreuil, Paris (FR); Fabien Faivre, Paris (FR); Benoît Ledoussal, Paris (FR); Frédéric Le Strat, Paris (FR); Sébastien Richard, Paris (FR); Christophe Simon, Paris (FR); Sophie Vomscheid, Paris (FR)

(73) Assignee: MUTABILIS, Paris (FR)

( * ) Notice: Subject to any disclaimer, the term of this patent is extended or adjusted under 35 U.S.C. 154(b) by 0 days.

(21) Appl. No.: 15/563,483

(22) PCT Filed: Mar. 30, 2016

(86) PCT No.: PCT/EP2016/056845
§ 371 (c)(1),
(2) Date: Sep. 29, 2017

(87) PCT Pub. No.: WO2016/156346
PCT Pub. Date: Oct. 6, 2016

(65) Prior Publication Data
US 2018/0086760 A1    Mar. 29, 2018

(30) Foreign Application Priority Data

Mar. 31, 2015  (EP) ..................................... 15305479
Jan. 22, 2016  (EP) ..................................... 16305059

(51) Int. Cl.
C07D 471/08    (2006.01)
A61K 31/439   (2006.01)
A61K 31/546   (2006.01)

(52) U.S. Cl.
CPC .......... *C07D 471/08* (2013.01); *A61K 31/439* (2013.01); *A61K 31/546* (2013.01)

(58) Field of Classification Search
CPC .................................................. C07D 471/08
See application file for complete search history.

(56) References Cited

U.S. PATENT DOCUMENTS

2018/0344826 A1   12/2018 Mahr et al.

FOREIGN PATENT DOCUMENTS

| EP | 3075734 | * | 5/2016 | ........... C07D 471/08 |
|----|---------|---|--------|--------|
| EP | 3075733 A1 | | 10/2016 | |
| EP | 3277267 A1 | | 2/2018 | |
| RU | 0002445314 C1 | | 3/2012 | |
| RU | 2012118247 A | | 11/2013 | |
| TN | 2017000416 A1 | | 1/2019 | |
| WO | 2013030733 A1 | | 3/2013 | |
| WO | 2013030735 A1 | | 3/2013 | |
| WO | 2013150296 A1 | | 10/2013 | |
| WO | 2013180197 A1 | | 12/2013 | |
| WO | 2014033560 A1 | | 3/2014 | |
| WO | 2014122468 A1 | | 8/2014 | |
| WO | 2014141132 A1 | | 9/2014 | |

OTHER PUBLICATIONS

"Syphilis-prevention", http://www.webmd.com/sexual-conditions/tc/syphilis-prevention?print=true, accessed Apr. 9, 2010, last updated Oct. 2, 2007 (Year: 2010).*
Greene. Protecting Groups in Organic Synthesis, Third Edition, 1999, pp. 17-23 (Year: 1999).*
International Search Report and Written Opinion in related International Application PCT/EP2016/056845 dated May 11, 2016, 8 pages.
European Search Report in related European Application EP15305479.6 dated Aug. 7, 2015, 7 pages.
Russian Office action issued in related Russian Application 2017133745/04(059514) dated Sep. 6, 2019, 6 pages.

* cited by examiner

*Primary Examiner* — Noble E Jarrell
(74) *Attorney, Agent, or Firm* — Thompson Coburn LLP; Steven M. Ritchey

(57) ABSTRACT

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

26 Claims, No Drawings

HETEROCYCLIC COMPOUNDS AND THEIR USE IN PREVENTING OR TREATING BACTERIAL INFECTIONS

CROSS-REFERENCE TO RELATED APPLICATIONS

This application is a U.S. National Phase application of PCT/EP2016/056845, filed on Mar. 30, 2016, claiming the benefit of European Application No. 15305479.6, filed on Mar. 31, 2015, and European Application No. 16305059.4, filed on Jan. 22, 2016, all of which are incorporated herein by reference in their entireties.

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

It has been described that there is a continuous evolution of antibacterial resistance which could lead to bacterial strains against which known antibacterial compounds are inefficient.

There is thus a need to provide effective compounds and composition that can overcome bacterial antibiotic resistance.

The objective of the present invention is to provide heterocyclic compounds that can be used as antibacterial agents and/or beta-lactamase inhibitors.

An objective of the present invention is also to provide heterocyclic compounds that can be used for the prevention or for the treatment of bacterial infections.

Another objective of the present invention is to provide heterocyclic compounds that can overcome bacterial antibiotic resistance.

An objective of the invention is also to provide pharmaceutical compositions comprising such heterocyclic compounds, optionally in combination with one or more other antibacterial agent, for the prevention or for the treatment of bacterial infections and which can overcome bacterial antibiotic resistance.

Other objectives will appear throughout the description of the invention.

The present invention thus provides a compound of formula (I)

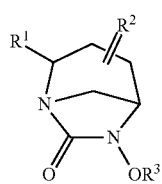

(I)

wherein $R^1$ represents a carbon-linked, unsubstituted or substituted by one or more $T^1$, aromatic, saturated, totally or partially unsaturated 4-, 5- or 6-membered heterocycle comprising at least one nitrogen atom; —CN; —C(O)NHQ$^1$; —C(O)NHOQ$^1$; —C(O)NH—NHQ$^1$; —C(O)O—NHQ$^1$; —C(O)OQ$^1$; —(CH$_2$)$_m$OC(O)Q$^1$; —(CH$_2$)$_m$OQ$^1$; —(CH$_2$)$_m$OC(O)Q$^1$; —(CH$_2$)$_m$OC(O)NQ$^1$Q$^2$; —(CH$_2$)$_m$—NHC(O)Q$^1$; —(CH$_2$)$_m$NHS(O)$_2$Q$^1$; —(CH$_2$)$_m$NHS(O)$_2$NQ$^1$Q$^2$; —(CH$_2$)$_m$NHC(O)NQ$^1$Q$^2$; —(CH$_2$)$_m$NHC(O)OQ$^1$; —(CH$_2$)$_m$—NHC(O)NQ$^1$Q$^2$; —(CH$_2$)$_m$NHQ$^3$; —(CH$_2$)$_m$NH—C(NHQ$^3$)=NQ$^4$; —(CH$_2$)$_m$NH—CH=NQ$^3$; —C(NHQ$^3$)=NQ$^4$;

$R^2$ represents O or NOQ$^5$;

$R^3$ represents SO$_3$H, CFHCO$_2$H or CF$_2$CO$_2$H;

$Q^1$ and $Q^2$, identical or different, independently represent a hydrogen atom; —(CH$_2$)$_p$NHQ$^3$; —(CH$_2$)$_p$—NH—C(NHQ$^3$)=NQ$^4$; (CH$_2$)$_p$—NH—CH=NQ$^3$; (CH$_2$)$_q$—C(NHQ$^3$)=NQ$^4$; —(CH$_2$)$_p$OQ$^3$; —(CH$_2$)$_q$CONHQ$^3$; or $Q^1$ and $Q^2$, unsubstituted or substituted by one or more $T^2$, identical or different, independently represent a $C_1$-$C_3$-alkyl; —(CH$_2$)$_n$-(4-, 5- or 6-membered heterocycle); or $Q^1$, $Q^2$ and the nitrogen atom to which they are bonded, form together a saturated or partially unsaturated 4-, 5- or 6-membered heterocycle comprising 1, 2 or 3 heteroatoms;

$Q^3$ and $Q^4$, identical or different, independently represent a hydrogen atom or a $C_1$-$C_3$-alkyl;

$Q^5$, unsubstituted or substituted by one or more $T^3$, represents $C_1$-$C_3$-alkyl; $C_1$-$C_3$-fluoroalkyl; —(CH$_2$)$_n$—$C_3$-$C_6$-cycloalkyl; —(CH$_2$)$_n$—$C_3$-$C_6$-cyclofluoroalkyl; —(CH$_2$)$_n$-(4-, 5- or 6-membered aromatic, saturated, totally or partially unsaturated heterocycle comprising at least one nitrogen atom); or $Q^5$ represents a hydrogen atom; (CH$_2$)$_p$OQ$^6$; —(CH$_2$)$_q$—CN; —(CH$_2$)$_p$OC(O)Q$^6$; —(CH$_2$)$_q$—C(O)OQ$^6$; —(CH$_2$)$_p$—OC(O)OQ$^6$; —(CH$_2$)$_p$—OC(O)NQ$^6$Q$^7$; —(CH$_2$)$_q$—C(O)NQ$^6$Q$^7$; —(CH$_2$)$_q$—C(O)NQ$^6$OQ$^7$; —(CH$_2$)$_q$—C(O)NQ$^6$—NQ$^6$Q$^7$; —(CH$_2$)$_p$—NQ$^6$C(O)Q$^7$; —(CH$_2$)$_p$NQ$^6$S(O)$_2$Q$^7$; —(CH$_2$)$_p$NQ$^6$S(O)$_2$NQ$^6$Q$^7$; —(CH$_2$)$_p$—NQ$^6$C(O)OQ$^6$; —(CH$_2$)$_p$—NQ$^6$C(O)NQ$^6$Q$^7$; —(CH$_2$)$_p$NQ$^6$Q$^7$; —(CH$_2$)$_p$—NH—C(NHQ$^3$)=NQ$^4$; —(CH$_2$)$_p$—NH—CH=NQ$^3$; (CH$_2$)$_q$—C(NHQ$^3$)=NQ$^4$;

$T^1$, identical or different, independently represents a fluorine atom; —(CH$_2$)$_n$OQ$^1$; —(CH$_2$)$_n$—CN; —(CH$_2$)$_n$OC(O)Q$^1$; —(CH$_2$)$_n$—C(O)OQ$^1$; —(CH$_2$)$_n$—OC(O)OQ$^1$; —(CH$_2$)$_n$—OC(O)NHQ$^1$; —(CH$_2$)$_n$—C(O)NHQ$^1$; —(CH$_2$)$_n$—C(O)NHOQ$^1$; —(CH$_2$)$_n$—C(O)NH—NHQ$^1$, ; —(CH$_2$)$_n$—NHC(O)Q$^1$; —(CH$_2$)$_n$NHS(O)$_2$Q$^1$; —(CH$_2$)$_n$NHS(O)$_2$NQ$^1$Q$^2$; —(CH$_2$)$_n$—NHC(O)OQ$^1$; —(CH$_2$)$_n$—NHC(O)NQ$^1$Q$^2$; —(CH$_2$)$_n$NHQ$^1$; —(CH$_2$)$_n$—NH—C(NHQ$^3$)=NQ$^4$; —(CH$_2$)$_n$—NH—CH=NQ$^3$; (CH$_2$)$_n$—C(NHQ$^3$)=NQ$^4$; or $T^1$, unsubstituted or substituted by one or more $T^2$, identical or different, independently represents $C_1$-$C_3$-alkyl; $C_1$-$C_3$-fluoroalkyl; O—$C_1$-$C_3$-fluoroalkyl; —(CH$_2$)$_n$-(4-, 5- or 6-membered aromatic, saturated, totally or partially unsaturated heterocycle comprising at least one nitrogen atom);

$T^2$, identical or different, independently represents OH; NH$_2$ or CONH$_2$;

$T^3$, identical or different, independently represents a fluorine atom; $C_1$-$C_3$-alkyl; $C_1$-$C_3$-fluoroalkyl; O—$C_1$-$C_3$-fluoroalkyl; —(CH$_2$)$_n$OQ$^6$—(CH$_2$)$_n$—$C_3$-$C_6$-cycloalkyl; —(CH$_2$)$_n$—$C_3$-$C_6$-cyclofluoroalkyl; —(CH$_2$)$_n$-heterocycle ; —(CH$_2$)$_n$—CN; —(CH$_2$)$_n$—OC(O)Q$^6$; —(CH$_2$)$_n$—C(O)OQ$^6$; —(CH$_2$)$_n$—OC(O)OQ$^6$; —(CH$_2$)$_n$—OC(O)NQ$^6$Q$^7$; —(CH$_2$)$_n$—C(O)NQ$^6$Q$^7$; —(CH$_2$)$_n$—C(O)NQ$^6$OQ$^7$; —(CH$_2$)$_n$—C(O)NQ$^6$—NQ$^6$Q$^7$; —(CH$_2$)$_n$—C(O)O—NHQ$^6$; —(CH$_2$)$_n$—NQ$^6$C(O)Q$^7$; —(CH$_2$)$_n$NQ$^6$S(O)$_2$Q$^7$; —(CH$_2$)$_n$NQ$^6$S(O)$_2$NQ$^6$Q$^7$; —(CH$_2$)$_n$—NQ$^6$C(O)OQ$^7$; —(CH$_2$)$_n$—NQ$^6$C(O)NQ$^6$Q$^7$; —(CH$_2$)$_n$NQ$^6$Q$^7$;

—(CH$_2$)$_n$—NH—C(NHQ$^3$)=NQ$^4$; —(CH$_2$)$_n$—NH—CH=NQ$^3$; —(CH$_2$)$_n$—C(NHQ$^3$)=NQ$^4$;

Q$^6$ and Q$^7$, identical or different, independently represent a hydrogen atom; C$_1$-C$_3$-alkyl; —(CH$_2$)$_p$NHQ$^3$; —(CH$_2$)$_p$—NH—C(NHQ$^3$)=NQ$^4$; —(CH$_2$)$_p$—NH—CH=NQ$^3$; —(CH$_2$)$_q$—C(NHQ$^3$)=NQ$^4$; —(CH$_2$)$_p$OQ$^3$; —(CH$_2$)$_q$C(O)NQ$^3$Q$^4$; —(CH$_2$)$_n$-(4-, 5- or 6-membered aromatic, saturated, totally or partially unsaturated heterocycle comprising at least one nitrogen atom); or Q$^6$, Q$^7$ and the nitrogen atom to which they are bonded form together a saturated or partially unsaturated 4-, 5- or 6-membered heterocycle comprising 1, 2 or 3 heteroatoms;

m, identical or different, independently represents 1 or 2;
n, identical or different, independently represents 0, 1, 2 or 3;
p, identical or different, independently represents 2 or 3;
q, identical or different, independently represents 1, 2 or 3;

wherein
any carbon atom present within a group selected from alkyl, cycloalkyl, fluoroalkyl, cyclofluoroalkyl and heterocycle can be oxidized to form a C=O group;
any sulphur atom present within a heterocycle can be oxidized to form a S=O group or a S(O)$_2$ group;
any nitrogen atom present within a heterocycle or present within group wherein it is trisubstituted thus forming a tertiary amino group, can be further quaternized by a methyl group;

and a pharmaceutically acceptable salt, a zwitterion, an optical isomer, a racemate, a diastereoisomer, an enantiomer, a geometric isomer or a tautomer thereof.

Preferably, the compound according to the invention is selected from the compounds of formulae (A) and (B)

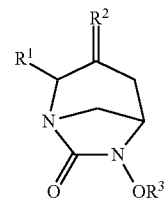

(A)

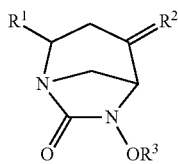

(B)

wherein R$^1$, R$^2$ and R$^3$ are defined according to formula (I).

Also preferably, the compound according to the invention is selected from the compounds of formulae (A1), (A2), (B1) and (B2)

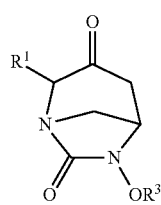

(A1)

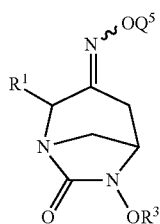

(A2)

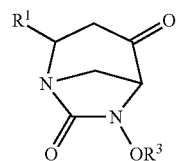

(B1)

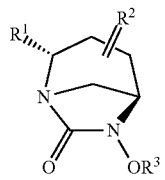

(B2)

wherein R$^1$, R$^3$ and Q$^5$ are defined according to formula (I).

More preferably, the compound according to the invention is selected from the compounds of formulae (I*), (A*), (B*), (A1*), (A2*), (B1*) and (B2*)

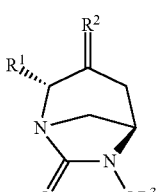

(I*)

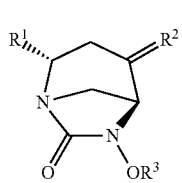

(A*)

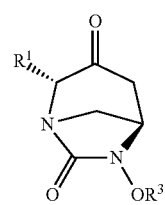

(B*)

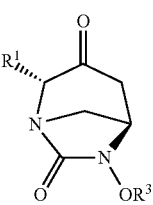

(A1*)

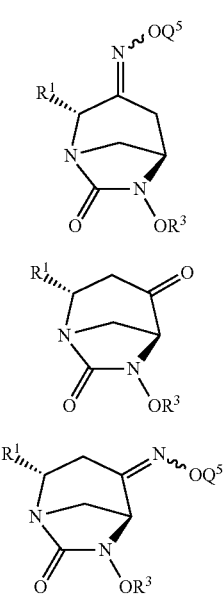

(A2*)

(B1*)

(B2*)

wherein $R^1$, $R^2$, $R^3$ and $Q^5$ are defined according to formula (I).

For the compounds according to the invention, $R^1$ preferably represents a carbon-linked, unsubstituted or substituted by one or more $T^1$, aromatic, saturated, totally or partially unsaturated 4-, 5- or 6-membered heterocycle comprising at least one nitrogen atom; —CN; —C(O)NHQ$^1$; —C(O)NHOQ$^1$; —C(O)NH—NHQ$^1$; —C(O)O—NHQ$^1$; —C(O)OQ$^1$; —(CH$_2$)OC(O)OQ$^1$; —(CH$_2$)$_2$OC(O)OQ$^1$; —(CH$_2$)OQ$^1$; —(CH$_2$)$_2$OQ$^1$; —(CH$_2$)OC(O)Q$^1$; —(CH$_2$)$_2$OC(O)Q$^1$; —(CH$_2$)—OC(O)NQ$^1$Q$^2$; —(CH$_2$)$_2$OC(O)NQ$^1$Q$^2$; —(CH$_2$)NHC(O)Q$^1$; —(CH$_2$)$_2$—NHC(O)Q$^1$; —(CH$_2$)NHS(O)$_2$Q$^1$; —(CH$_2$)$_2$NHS(O)$_2$Q$^1$; —(CH$_2$)NHS(O)$_2$NQ$^1$Q$^2$; —(CH$_2$)$_2$NHS(O)$_2$NQ$^1$Q$^2$; —(CH$_2$)NHC(O)OQ$^1$; —(CH$_2$)$_2$NHC(O)OQ$^1$; —(CH$_2$)NHC(O)NQ$^1$Q$^2$; —(CH$_2$)$_2$NHC(O)NQ$^1$Q$^2$. More preferably, $R^1$ represents a carbon-linked, unsubstituted or substituted by one or more $T^1$, aromatic, saturated, totally or partially unsaturated 4-, 5- or 6-membered heterocycle comprising at least one nitrogen atom; —CN; —C(O)NHQ$^1$; —C(O)NHOQ$^1$; —C(O)NH—NHQ$^1$; —(CH$_2$)$_2$OQ$^1$.

For the compounds according to the invention, $R^1$ represents equally preferably —(CH$_2$)NHQ$^3$; —(CH$_2$)$_2$NHQ$^3$; —(CH$_2$)NH—C(NHQ$^3$)=NQ$^4$; —(CH$_2$)$_2$NH—C(NHQ$^3$)=NQ$^4$; —(CH$_2$)NH—CH=NQ$^3$; —(CH$_2$)$_2$NH—CH=NQ$^3$; —C(NHQ$^3$)=NQ$^4$. More preferably, $R^1$ represents —(CH$_2$)NHQ$^3$; —(CH$_2$)NH—C(NHQ$^3$)=NQ$^4$, in particular $R^1$ represents —(CH$_2$)NH$_2$ or —(CH$_2$)NH—C(NH$_2$)=NH.

For the compounds according to the invention, $R^1$ may represent a carbon-linked, unsubstituted or substituted by one or more $T^1$, aromatic, saturated, totally or partially unsaturated 4-, 5- or 6-membered heterocycle that comprises at least one nitrogen atom. Such a 4-, 5- or 6-membered heterocycle may further comprise one or more heteroatoms, for example 1, 2 or 3 further heteroatoms, preferably selected from N, O, S, S(O) or S(O)$_2$.

For the compounds according to the invention, $R^3$ preferably represents SO$_3$H or CF$_2$COOH.

For the compounds according to the invention, $Q^1$ and $Q^2$ and the nitrogen atom to which they are bonded, may form together a saturated or partially unsaturated 4-, 5- or 6-membered heterocycle comprising 1, 2 or 3 heteroatoms. The resulting 4-, 5- or 6-membered heterocycle thus comprises the nitrogen atom bonded to $Q^1$ and $Q^2$ and one or two further optional heteroatoms.

For the compounds according to the invention, $Q^1$ and $Q^2$, identical or different, preferably represent H; methyl ; —CH$_2$—CH$_2$—NH$_2$; —CH$_2$—CH$_2$—NH—CNH$_2$=NH; —CH$_2$—CH$_2$—NH—CH=NH; —CH$_2$—C(NH$_2$)=NH; —CH$_2$—CH$_2$—OH; —CH$_2$—CONH$_2$; a —(CH$_2$)$_n$-(saturated, partially or totally unsaturated or aromatic 4-, 5- or 6-membered heterocycle comprising at least one nitrogen atom) wherein the heterocycle can be substituted by one or more $T^2$, and n and $T^2$ are defined according to formula (I).

For the compounds according to the invention, $Q^1$ and $Q^2$, identical or different, more preferably represent H; methyl ; —CH$_2$—CH$_2$—NH$_2$; —CH$_2$—CH$_2$—NH—CNH$_2$=NH; —CH$_2$—CH$_2$—NH—CH=NH; —CH$_2$—C(NH$_2$)=NH; —CH$_2$—CH$_2$—OH; —CH$_2$—CONH$_2$; a saturated, partially or totally unsaturated or aromatic 4-, 5- or 6-membered heterocycle comprising one nitrogen atom, wherein the heterocycle can be substituted by one or more $T^3$ that is defined according to formula (I).

For the compounds according to the invention, $Q^3$ and $Q^4$, identical or different, preferably represent H or methyl.

For the compounds according to the invention, $Q^6$ and $Q^7$ and the nitrogen atom to which they are bonded, may form together a saturated or partially unsaturated 4-, 5- or 6-membered heterocycle comprising 1, 2 or 3 heteroatoms. The resulting 4-, 5- or 6-membered heterocycle thus comprises the nitrogen atom bonded to $Q^6$ and $Q^7$ and one or two further optional heteroatoms.

Preferably, in the compounds of formula (I), (A), (B), (A1), (A2), (B1), (B2), (I*), (A*), (B*), (A1*), (A2*), (B1*) and (B2*) according to the invention:

$R^1$ represents —C(O)NHQ$^1$; —C(O)NHOQ$^1$; —C(O)NH—NHQ$^1$; —C(O)OQ$^1$; —(CH$_2$)$_m$NHQ$^3$; —(CH$_2$)$_m$NH—C(NHQ$^3$)=NQ$^4$ $Q^1$ and $Q^3$ are as defined above and preferably represent H or C$_1$-C$_3$-alkyl;

m is as defined above;

$R^2$ represents O or NOQ$^5$;

$Q^5$ is as defined above and preferably represents —(CH$_2$)$_q$—C(O)NQ$^6$Q$^7$; —(CH$_2$)$_q$—C(O)NQ$^6$OQ$^7$; —(CH$_2$)$_q$—C(O)NQ$^6$—NQ$^6$Q$^7$; —(CH$_2$)$_p$NQ$^6$Q$^7$; —(CH$_2$)$_p$—NH—C(NHQ$^3$)=NQ$^4$ p and q are as defined above;

$Q^4$, $Q^6$ and $Q^7$, are as defined above and preferably identical or different, independently represent a hydrogen atom; C$_1$-C$_3$-alkyl.

Preferably, in the compounds of formula (I), (A), (B), (A1), (A2), (B1), (B2), (I*), (A*), (B*), (A1*), (A2*), (B1*) and (B2*) according to the invention:

$R^1$ represents —C(O)NHQ$^1$; —C(O)OQ$^1$; —(CH$_2$)$_m$NHQ$^3$ $Q^1$ and $Q^3$ are as defined above and preferably represent H or C$_1$-C$_3$-alkyl;

m is as defined above, preferably 1;

$R^2$ represents O or NOQ$^5$;

$Q^5$ is as defined above and preferably represents —(CH$_2$)$_q$—C(O)NQ$^6$Q$^7$; —(CH$_2$)$_p$NQ$^6$Q$^7$ p and q are as defined above, preferably 1 or 2;

$Q^4$, $Q^6$ and $Q^7$, are as defined above and preferably identical or different, independently represent a hydrogen atom; C$_1$-C$_3$-alkyl.

The invention relates also to compounds of formula

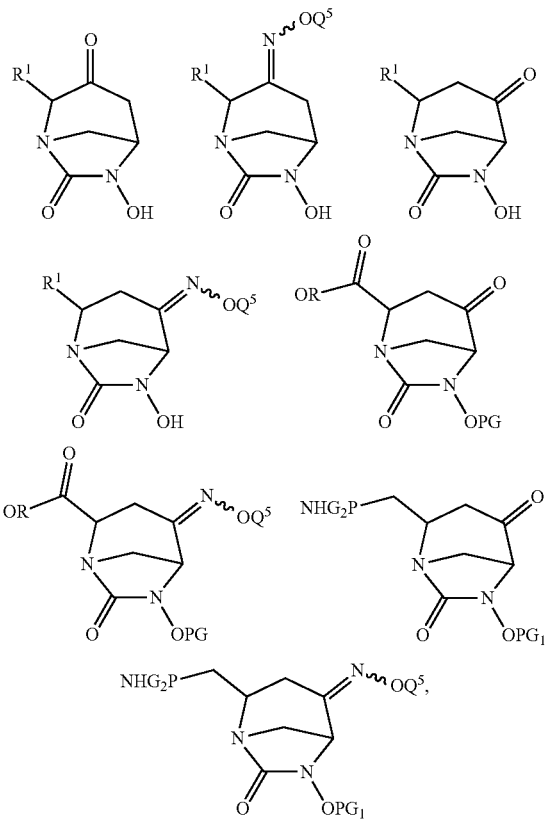

preferably of formula

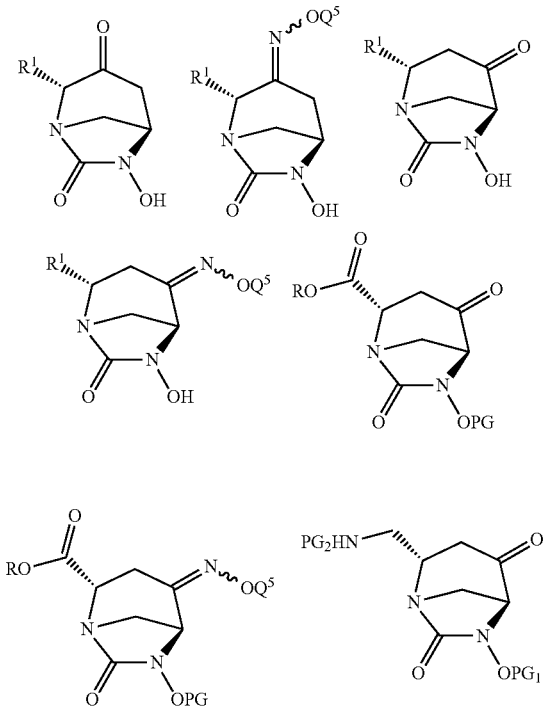

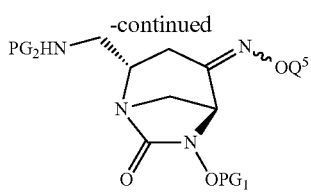

wherein $Q^5$ and $R^1$ are as described above, R represents alkyl, especially $C_1$-$C_6$ alkyl, or benzyl, and PG, $PG_1$ and $PG_2$, identical or different, are protective groups, for example chosen among allyl, benzyl, tertbutyldimethylsilyl (TBDMS), tert-butoxycarbonyl (Boc), etc. The compounds are especially intermediates compounds for the preparation of compounds of formula (I), (A), (B), (A1), (A2), (B1), (B2), (I*), (A*), (B*), (A1*), (A2*), (B1*) and (B2*) according to the invention.

The term "alkyl", as used herein, refers to an aliphatic-hydrocarbon group which may be straight or branched, having 1 to 3 carbon atoms in the chain unless specified otherwise. Preferred alkyl groups have 1 or 2 carbon atoms in the chain. Specific examples of alkyl groups include, but are not limited to, methyl, ethyl, n-propyl, isopropyl. Preferably, the alkyl group is methyl or ethyl.

The term "fluoroalkyl", as used herein, refers to an alkyl group substituted with at least one fluorine atom. The term "alkyl" is as defined above. Specific examples of fluoroalkyl groups include but are not limited to trifluoromethyl, difluoromethyl, fluoromethyl.

The term "cycloalkyl" refers to a saturated monocyclic or bicyclic non-aromatic hydrocarbon ring of 3 to 6 carbon atoms, preferably 3 to 4 carbon atoms, which can comprise one or more unsaturation. Specific examples of monocyclic cycloalkyl groups include cyclopropyl, cyclobutyl, cyclopentyl, cyclohexyl. Preferably, the cycloalkyl group is cyclopropyl or cyclobutyl.

The term "fluorocycloalkyl" refers to a cycloalkyl group substituted with at least one fluorine atom. The term "cycloalkyl" is as defined above. Specific examples of fluorocycloalkyl groups include fluorocyclopropyl, difluorocyclopropyl, fluorocyclobutyl, difluorocyclobutyl.

The term "heterocycle", as used herein and without contrary definition specifically mentioned, either alone or in combination with another radical, refers to a monocyclic saturated, partially or totally unsaturated or aromatic hydrocarbon radical, preferably to a 4- to 10-membered hydrocarbon radical, comprising at least one heteroatom, such as N, O, S, S(O) or S(O)$_2$. Preferably, the heterocycle is a monocyclic saturated, partially or totally unsaturated or aromatic hydrocarbon radical, preferably a 4- to 6-membered hydrocarbon radical, comprising at least one nitrogen atom and at least one further heteroatom, such as N, O, S, S(O) or S(O)$_2$. The carbon atoms of the heterocycle can also be oxidized to form a C(O) group. Suitable heterocycles are also disclosed in the Handbook of Chemistry and Physics, 76$^{th}$ Edition, CRC Press, Inc., 1995-1996, pages 2-25 to 2-26. Examplary heterocycle groups include, but are not limited to, azetidinyl, oxetanyl, oxazolyl, oxazolidinyl, oxadiazolyl, pyrrolyl, pyrrolidinyl, pyridyl, tetrahydropyridinyl, piperidinyl, morpholinyl, pyrazolyl, pyrimidinyl, pyrazinyl, tetrazolyl, imidazolyl, thienyl, thiazolyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazol-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, tetrahydropyranyl. Preferably, in the compounds according to the invention, the heterocycle is linked to the structure of the compounds by a carbon atom of the heterocycle (also said carbon-linked heteroatom).

Moreover some compounds according to this invention may contain a basic amino group and thus may form an inner zwitterionic salt (or zwitterion) with the acidic group ($R^3$)—$OSO_3H$, —$OCFHCO_2H$ or —$OCF_2CO_2H$ and such inner zwitterionic salts are also included in this invention.

The expression "optionally substituted" means "non-substituted or substituted by chemical groups that are further defined" or "unsubstituted or substituted chemical groups that are further defined".

The term "racemate" is employed herein to refer to an equal amount of two specific enantiomers.

The term "enantiomer" is employed herein to refer to one of the two specific stereoisomers which is a non-superimposable mirror image with one other but is related to one other by reflection.

The compounds according to the invention may include one or more asymmetric carbon atoms and may thus exist in the form of optical isomers as well as in the form of racemic or non-racemic mixtures thereof. The compounds according to the invention can be utilized as a single isomer or as a mixture of stereochemical isomeric forms. Diastereoisomers, i.e., non-superimposable stereochemical isomers can be separated by conventional means such as chromatography, distillation, crystallization or sublimation. The optical isomers (enantiomers) can be obtained by using optically active starting materials, by resolution of the racemic mixtures according to conventional processes, for example by formation of diastereoisomeric salts by treatment with an optically active acid or base or by using chiral chromatography column.

As used herein, the expression "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention can be synthesized from the parent compound which comprises a basic or an acidic moiety, by conventional chemical methods. Furthermore, the expression "pharmaceutically acceptable salt" refers to relatively non-toxic, inorganic and organic acid or base addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, hydroiodide, sulfamate, sulfate, bisulfate, phosphate, nitrate, acetate, propionate, succinate, oxalate, valerate, oleate, palmitate, stearate, laurate, borate, benzoate, lactate, tosylate, citrate, maleate, fumarate, tartrate, naphthylate, mesylate, glucoheptanate, glucoronate, glutamate, lactobionate, malonate, salicylate, methylenebis-b-hydroxynaphthoate, gentisic acid, isethionate, di-p-toluoyltartrate, ethanesulfonate, benzenesulfonate, cyclohexyl sulfamate, quinateslaurylsulfonate salts, and the like. Examples of base addition salts include ammonium salts such as tromethamine, meglumine, epolamine, etc, metal salts such as sodium, lithium, potassium, calcium, zinc or magnesium salts with organic bases such as dicyclohexylamine salts, N-methyl-D-glucamine. Lists of suitable salts may be found in Remington's Pharmaceutical Sciences, 17th ed., Mack Publishing Company, Easton, Pa., 1985, p. 1418, P. H. Stahl, C. G. Wermuth, Handbook of Pharmaceutical salts—Properties, Selection and Use, Wiley-VCH, 2002 and S. M. Berge et al. "Pharmaceutical Salts" J. Pharm. Sci, 66: p. 1-19 (1977).

Compounds according to the invention also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described above and are not limited to $^2H$, $^3H$, $^{11}C$, $^{13}C$, $^{14}C$, $^{18}F$, $^{19}F$, $^{13}N$, $^{15}N$, $^{33}S$, $^{34}S$, $^{35}$, $^{36}S$, $^{17}O$ or $^{18}O$. Isotopically-labeled compounds are useful in drug and/or substrate tissue distribution studies. Substitution with heavier isotopes such as deuterium ($^2H$) affords greater metabolic stability (for example increased in vivo half-life or reduced dosage requirements). Isotopically-labeled compounds are prepared by any suitable method or by processes using an appropriate isotopically-labeled reagent in replacement of the non-labeled reagent otherwise employed.

The invention provides compounds having antibacterial properties and/or compounds acting as β-lactamase inhibitors.

The invention also provides a process for the preparation of a compound according to the invention. In particular the invention provides a process for the preparation of compound selected within the compounds of formulae (I), (A), (B), (A1), (A2), (B1), (B2), (I*), (A*), (B*), (A1*), (A2*), (B1*) and (B2*) according to the invention.

General processes according to the invention are represented in schemes 1 to 3 wherein $R^1$ represents various substituents.

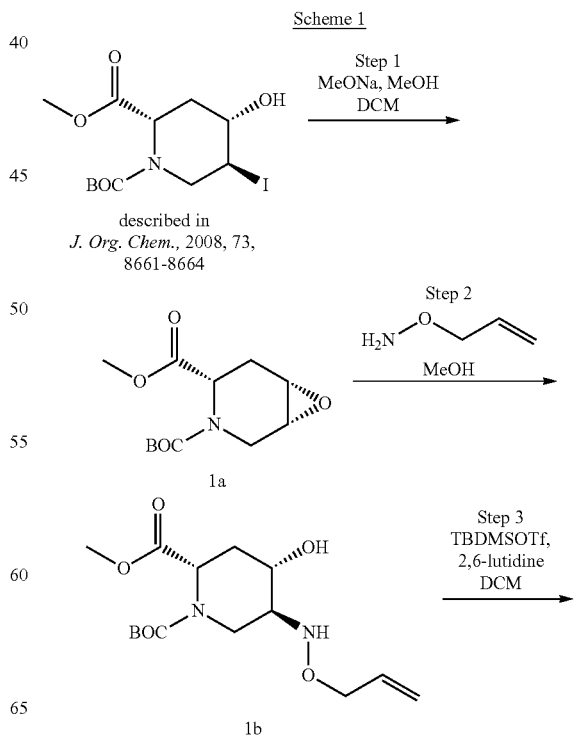

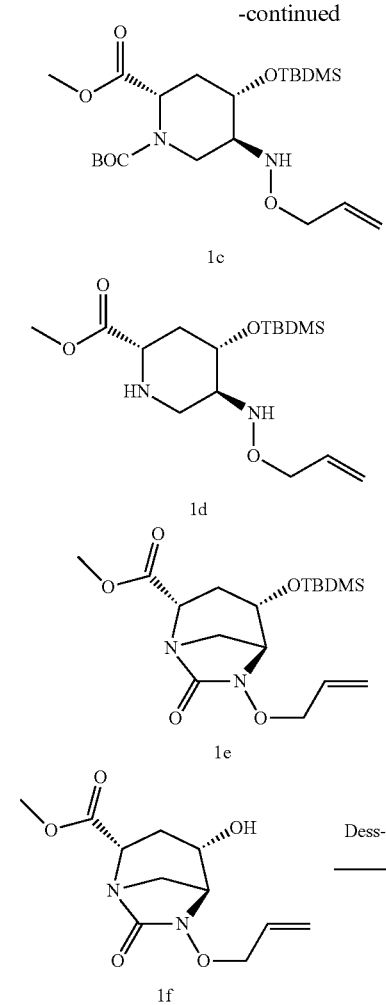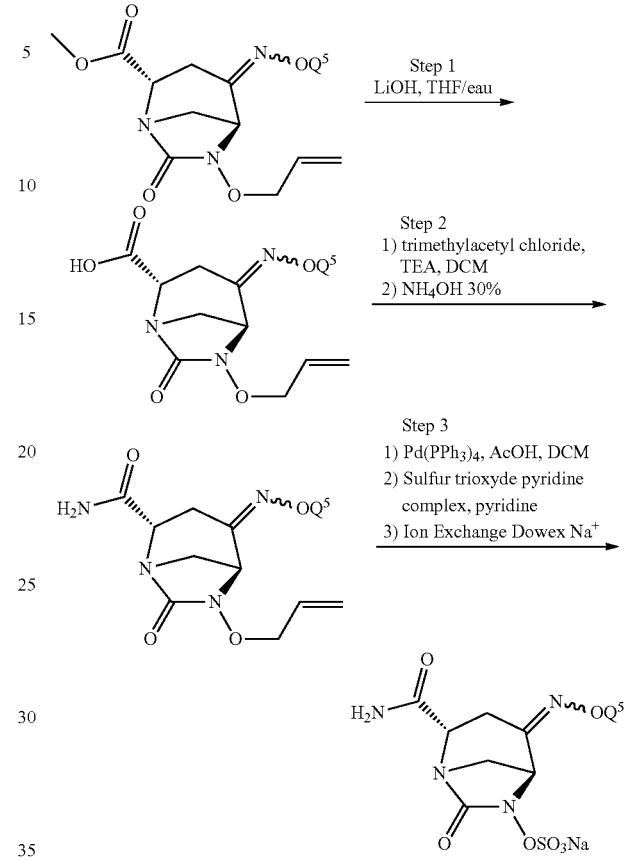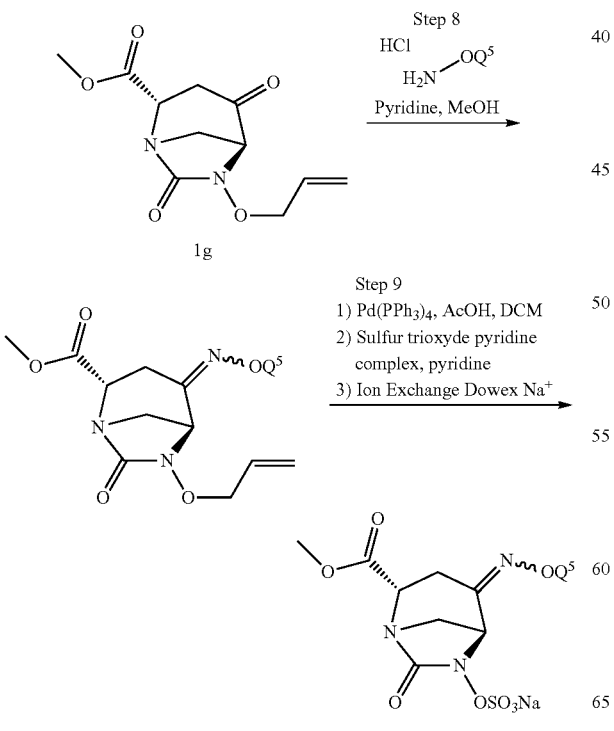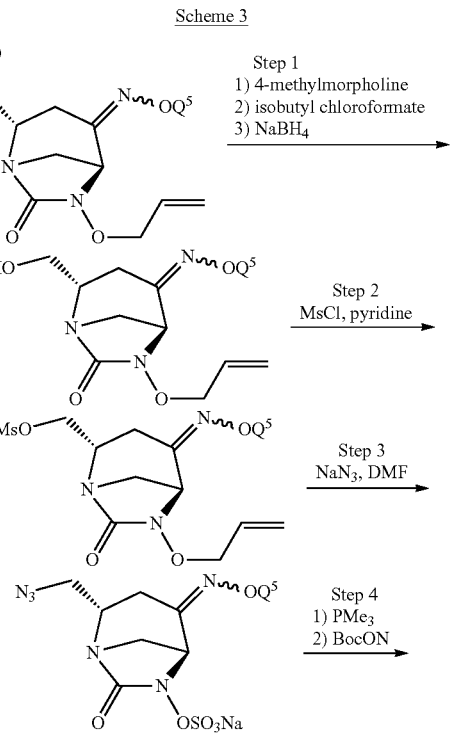

13

-continued

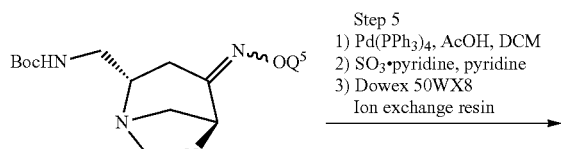

Step 5
1) Pd(PPh₃)₄, AcOH, DCM
2) SO₃·pyridine, pyridine
3) Dowex 50WX8
Ion exchange resin

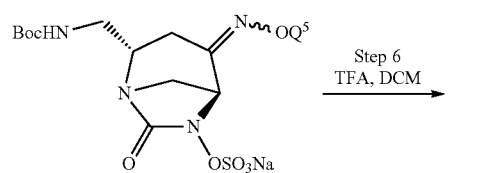

Step 6
TFA, DCM

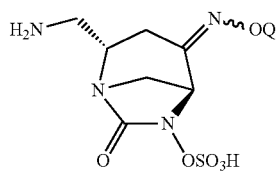

Scheme 4

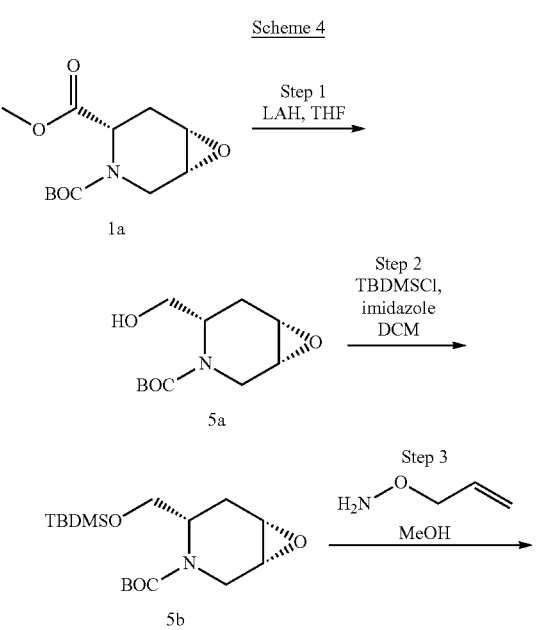

Step 1
LAH, THF

Step 2
TBDMSCl, imidazole
DCM

Step 3
H₂N—O—allyl
MeOH

Step 4
TBDMSOTf,
2,6-lutidine
DCM

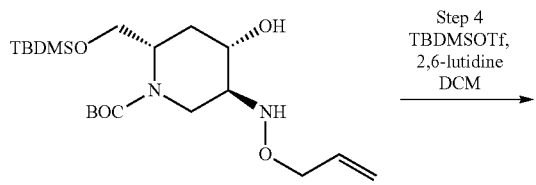

Step 5
TMSI, DCM

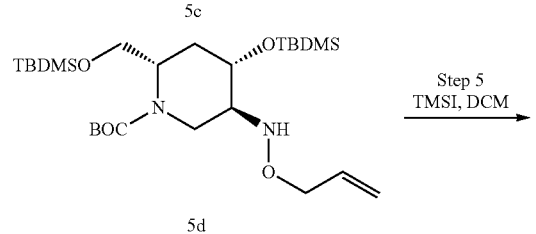

14

-continued

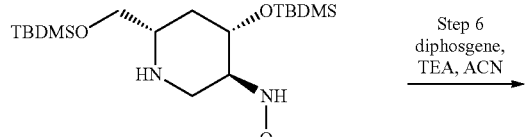

5e

Step 6
diphosgene,
TEA, ACN

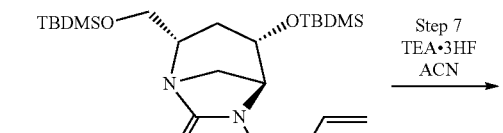

5f

Step 7
TEA·3HF
ACN

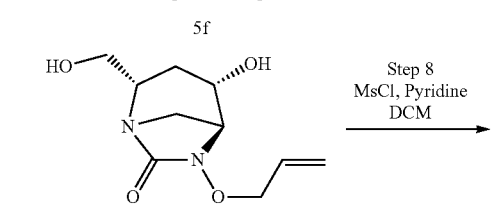

5g

Step 8
MsCl, Pyridine
DCM

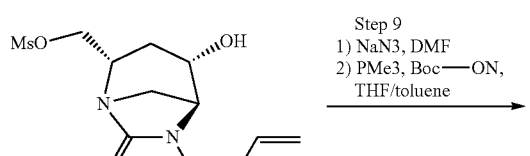

5h

Step 9
1) NaN₃, DMF
2) PMe₃, Boc—ON,
THF/toluene

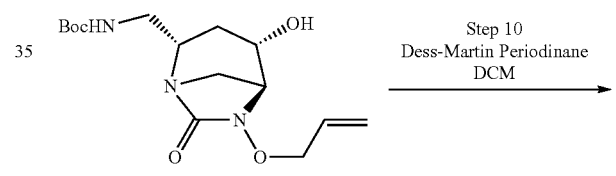

5i

Step 10
Dess-Martin Periodinane
DCM

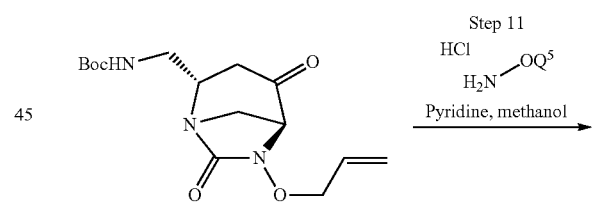

5j

Step 11
HCl
H₂N—OQ⁵
Pyridine, methanol

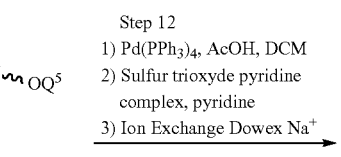

Step 12
1) Pd(PPh₃)₄, AcOH, DCM
2) Sulfur trioxyde pyridine
complex, pyridine
3) Ion Exchange Dowex Na⁺

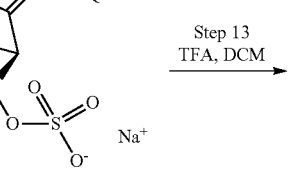

Step 13
TFA, DCM

-continued

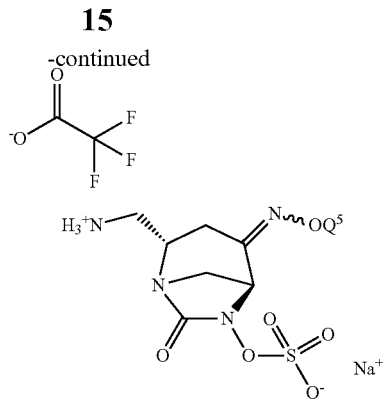

The processes of schemes 1 to 4 can be adapted for preparing further compounds according to the invention. Further processes for the preparation of compounds according to the invention can be derived from the processes of schemes 1 to 4.

The invention also provides the use of the compounds according to the invention in the control of bacteria. The compound according to the invention is then usually used in combination with at least one pharmaceutically acceptable excipient.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also provides a composition, preferably a pharmaceutical composition, comprising at least one compound according to the invention in mixture with a pharmaceutically acceptable excipient. The composition according to the invention may thus comprise at least one compound selected from compounds of formulae (I), (A), (B), (A1), (A2), (B1), (B2), (I*), (A*), (B*), (A1*), (A2*), (B1*) and (B2*) in mixture with a pharmaceutically acceptable excipient.

The composition according to the invention can further comprise at least one or more antibacterial agent(s), preferably at least one of these antibacterial agents is a beta-lactam.

The term "beta-lactam" or "β-lactam" refers to antibacterial compounds comprising a β-lactam unit, i.e. a β-lactam chemical group or moiety.

The term "pharmaceutically acceptable carrier" or "pharmaceutically acceptable excipient" is employed for any excipient, solvent, dispersion medium, absorption retardant, diluent or adjuvant etc., such as preserving or antioxidant agents, fillers, binders, disintegrating agents, wetting agents, emulsifying agents, suspending agents, solvents, dispersion media, coatings, antibacterial agents, isotonic and absorption delaying agents and the like, that does not produce a secondary reaction, for example an allergic reaction, in humans or animals. Typical, non-limiting examples of excipients include mannitol, lactose, magnesium stearate, sodium saccharide, talcum, cellulose, sodium crosscarmellose, glucose, gelatin, starch, lactose, dicalcium phosphate, sucrose, kaolin, magnesium carbonate, wetting agents, emulsifying agents, solubilizing agents, sterile water, saline, pH buffers, non-ionic surfactants, lubricants, stabilizing agents, binding agents and edible oils such as peanut oil, sesame oils and the like. In addition, various excipients commonly used in the art may be included. Pharmaceutically acceptable carriers or excipients are well known to a person skilled in the art, and include those described in Remington's Pharmaceutical Sciences (Mack Publishing Company, Easton, USA, 1985), Merck Index (Merck & Company, Rahway, N.J.), Gilman et al (Eds. The pharmacological basis of therapeutics, $8^{th}$ Ed., Pergamon press., 1990). Except insofar as any conventional media or adjuvant is incompatible with the active ingredient according to the invention, its use in the therapeutic compositions is contemplated.

The expression "antibacterial agent" as used herein, refers to any substance, compound or their combination capable of inhibiting, reducing or preventing growth of bacteria, inhibiting or reducing ability of bacteria to produce infection in a subject, or inhibiting or reducing ability of bacteria to multiply or remain infective in the environment, or decreasing infectivity or virulence of bacteria.

The antibacterial agent can be selected among the following families: aminoglycosides, beta-lactams, glycylcyclines, tetracyclines, quinolones, fluoroquinolones, glycopeptides, lipopeptides, macrolides, ketolides, lincosamides, streptogramins, oxazolidinones and polymyxins alone or in mixture. Preferably, the further antibacterial agent is selected among the beta-lactam families, and more preferably among penicillin, cephalosporins, penems, carbapenems and monobactam, alone or in mixture.

Among the penicillin the antibacterial agent is preferably selected in the group consisting of amoxicillin, ampicillin, azlocillin, mezocillin, apalcillin, hetacillin, bacampicillin, carbenicillin, sulbenicillin, temocillin, ticarcillin, piperacillin, mecillinam, pivmecillinam, methicillin, ciclacillin, talampacillin, aspoxicillin, oxacillin, cloxacillin, dicloxacillin, flucloxacillin, nafcillin, and pivampicillin, alone or in mixture.

Among the cephalosporin, the antibacterial agent is preferably selected in the group consisting of cefatriazine, cefazolin, cefoxitin, cephalexin, cephradine, ceftizoxime, cephacetrile, cefbuperazone, cefprozil, ceftobiprole, ceftobiprole medocaril, ceftaroline, ceftaroline fosaminyl, cefalonium, cefminox, ceforanide, cefotetan, ceftibuten, cefcapene pivoxil, cefditoren pivoxil, cefdaloxime cefroxadine, ceftolozane and S-649266, cephalothin, cephaloridine, cefaclor, cefadroxil, cefamandole, cefazolin, cephalexin, cephradine, ceftizoxime, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidine, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbef, and latamoxef, alone or in mixture.

Among the carbapenem, the antibacterial agent is preferably selected in the group consisting of imipenem, doripenem, meropenem, biapenem, ertapenem and panipenem, alone or in mixture.

Among the monobactam, the antibacterial agent is preferably selected in the group consisting of aztreonam, tigemonam, carumonam, BAL30072 and nocardicin A, alone or in mixture.

The present invention also relates to a composition comprising at least a compound of formulae (I), (A), (B), (A1), (A2), (B1), (B2), (I*), (A*), (B*), (A1*), (A2*), (B1*) and (B2*) according to the invention and ceftazidime.

The present invention also provides a kit comprising:
a pharmaceutical composition according to the invention, and
at least one other composition comprising one or more antibacterial agents, preferably at least one of these antibacterial agents is a beta-lactam.

The two compositions can each be prepared separately with one specific pharmaceutically acceptable carrier, and can then be mixed, especially extemporaneously.

The present invention also relates to a kit comprising:
a pharmaceutical composition comprising at least a compound of formulae (I), (A), (B), (A1), (A2), (B1), (B2), (I*), (A*), (B*), (A1*), (A2*), (B1*) and (B2*) according to the invention; and
a pharmaceutical composition comprising ceftazidime.

The present invention also refers to a compound selected within the compounds of formulae (I), (A), (B), (A1), (A2), (B1), (B2), (I*), (A*), (B*), (A1*), (A2*), (B1*) and (B2*) according to the invention for its use as a medicine.

The present invention also refers to a compound selected within the compounds of formulae (I), (A), (B), (A1), (A2), (B1), (B2), (I*), (A*), (B*), (A1*), (A2*), (B1*) and (B2*) according to the invention for its use for the preparation of a medicine.

The present invention also refers to a compound selected within the compounds of formulae (I), (A), (B), (A1), (A2), (B1), (B2), (I*), (A*), (B*), (A1*), (A2*), (B1*) and (B2*) according to the invention for its use as an antibacterial agent.

The present invention also refers to the use of a compound selected within the compounds of formulae (I), (A), (B), (A1), (A2), (B1), (B2), (I*), (A*), (B*), (A1*), (A2*), (B1*) and (B2*) according to the invention or to the use of a pharmaceutical composition according to the invention for the preparation of an antibacterial agent comprising medicine.

The present invention also refers to the use of a compound selected within the compounds of formulae (I), (A), (B), (A1), (A2), (B1), (B2), (I*), (A*), (B*), (A1*), (A2*), (B1*) and (B2*) according to the invention or to the use of a pharmaceutical composition according to the invention for the preparation of a beta-lactamase inhibitor comprising medicine.

The present invention also refers to the use of a compound selected within the compounds of formulae (I), (A), (B), (A1), (A2), (B1), (B2), (I*), (A*), (B*), (A1*), (A2*), (B1*) and (B2*) according to the invention or to the use of a pharmaceutical composition according to the invention for the preparation of a medicine comprising an antibacterial agent and a beta-lactamase inhibitor.

The present invention also refers to the use of a compound selected within the compounds of formulae (I), (A), (B), (A1), (A2), (B1), (B2), (I*), (A*), (B*), (A1*), (A2*), (B1*) and (B2*) according to the invention or to the use of a pharmaceutical composition according to the invention or to the use of a kit according to the invention for the treatment or for the prevention of at least one bacterial infection.

The present invention also refers to the use of a compound selected within the compounds of formulae (I), (A), (B), (A1), (A2), (B1), (B2), (I*), (A*), (B*), (A1*), (A2*), (B1*) and (B2*) according to the invention or to the use of a pharmaceutical composition according to the invention or to the use of a kit according to the invention for the preparation of a medicine useful in the treatment or in the prevention of at least one bacterial infection.

The terms "prevention", "prevent" and "preventing" as used herein are intended to mean the administration of a compound or composition according to the invention in order to prevent infection by bacteria or to prevent occurrence of related infection and/or diseases. The terms "prevention", "prevent" and "preventing" also encompass the administration of a compound or composition according to the present invention in order preventing at least one bacterial infection, by administration to a patient susceptible to be infected, or otherwise at a risk of being infected by this bacteria.

The terms "treatment", "treat" and "treating" as used herein are intended to mean in particular the administration of a treatment comprising a compound or composition according to the invention to a patient suffering from an infection. The terms "treatment", "treat" and "treating" as used herein, also refer to administering a compound or composition according to the invention, optionally in combination with one or more further antibacterial agent, in order:

to reduce or to eliminate either bacterial infection or one or more symptoms associated with a bacterial infection, or to retard the progression of a bacterial infection or of one or more symptoms associated with a bacterial infection, or to reduce the severity of a bacterial infection or of one or more symptoms associated with a bacterial infection, or to suppress the clinical manifestation of a bacterial infection, or to suppress the manifestation of adverse symptoms caused by a bacterial infection.

The expression "infection" or "bacterial infection" as used herein, include the presence of bacteria, in or on a subject, which, if its growth were inhibited, would result in a benefit to the subject. As such, the term "infection" or "bacterial infection" in addition to referring to the presence of bacteria also refer to normal flora, which is not desirable. The term "infection" includes infection caused by bacteria. Examples of such bacterial infections are urinary tract infection (UTI), kidney infections (pyelonephritis), gynecological and obstetrical infections, respiratory tract infection (RTI), acute exacerbation of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, chlamydia, skin infections, bacteremia.

The term "growth" as used herein, refers to the growth of one or more microorganisms and includes reproduction or population expansion of a microorganism, such as bacteria. The term also includes maintenance of on-going metabolic processes of a microorganism, including processes that keep the microorganism alive.

According to the invention, bacteria are chosen amongst gram-positive bacteria or gram-negative bacteria, preferably gram-negative bacteria. According to the invention, bacteria can be also chosen among bacteria producing "beta-lactamase" or "β-lactamase". These bacteria are well known by the person skilled in the art. The term "beta-lactamase" or "β-lactamase" as used herein, refers to any enzyme or protein or any other substance that is able to break down a beta-lactam ring. The term "beta-lactamase" or "β-lactamase" includes enzymes that are produced by bacteria and that have the ability to hydrolyze, either partially or completely, the beta-lactam ring present in a compound such as an antibacterial agent.

Among the gram-positive bacteria, the bacteria according to the invention is preferably chosen among *Staphylococcus*,

*Streptococcus, Staphylococcus* species (including *Staphylococcus aureus, Staphylococcus epidermidis*), *Streptococcus* species (including *Streptococcus pneumonia, Streptococcus agalactiae*), *Enterococcus* species (including *Enterococcus faecalis* and *Enterococcus faecium*).

Among the gram-negative bacteria, the bacteria according to the invention is preferably chosen among *Acinetobacter* species (including *Acinetobacter baumannii*), *Citrobacter* species, *Escherichia* species (including *Escherichia coli*), *Haemophilus influenza, Morganella morganii, Klebsiella* species (including *Klebsiella pneumonia*), *Enterobacter* species (including *Enterobacter cloacae*), *Neisseria gonorrhoeae, Burkholderia* species (including *Burkholderia cepacia*), (*Proteus* species (including *Proteus mirabilis*), *Serratia* species (including *Serratia marcescens*), *Pseudomonas aeruginosa*.

The invention thus preferably refers to a compound selected within the compounds of formulae (I), (A), (B), (A1), (A2), (B1), (B2), (I*), (A*), (B*), (A1*), (A2*), (B1*) and (B2*) according to the invention or to a pharmaceutical composition according to the invention or to a kit according to the invention for its use for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to the use of a compound selected within the compounds of formulae (I), (A), (B), (A1), (A2), (B1), (B2), (I*), (A*), (B*), (A1*), (A2*), (B1*) and (B2*) according to the invention or to a pharmaceutical composition according to the invention for the preparation of a medicine for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to a kit according to the invention, for its simultaneous, separated or sequential administration to a patient in need thereof in the treatment or in the prevention of bacterial infections, preferably caused by bacteria producing one or more beta-lactamases. Preferably, the bacteria are chosen amongst gram-positive bacteria or gram-negative bacteria, more preferably gram-negative bacteria.

The present invention also refers to a compound selected within the compounds of formulae (I), (A), (B), (A1), (A2), (B1), (B2), (I*), (A*), (B*), (A1*), (A2*), (B1*) and (B2*) according to the invention for its use in combination with one or more further antibacterial agents, preferably at least one of the further antibacterial agents being a beta lactam compound, for the treatment or for the prevention of bacterial infections, preferably caused by bacteria producing one or more beta-lactamases. Preferably, the bacteria are chosen amongst gram-positive bacteria or gram-negative bacteria, more preferably gram-negative bacteria, and wherein a compound selected within the compounds of formulae (I), (A), (B), (A1), (A2), (B1), (B2), (I*), (A*), (B*), (A1*), (A2*), (B1*) and (B2*) according to the invention and the further antibacterial agent are administered simultaneously, separately or sequentially.

The present invention also refers to the use of a compound selected within the compounds of formulae (I), (A), (B), (A1), (A2), (B1), (B2), (I*), (A*), (B*), (A1*), (A2*), (B1*) and (B2*) according to the invention or of a pharmaceutical composition according to the invention or of a kit according to the invention for the prevention or for the treatment of bacterial infections, preferably of a bacterial infection, preferably caused by bacteria producing one or more beta-lactamases. Preferably, the bacteria are chosen amongst gram-positive bacteria or gram-negative bacteria, more preferably gram-negative bacteria.

The present invention also relates to a method for the treatment or prevention of bacterial infections, preferably caused by bacteria producing one or more beta-lactamases comprising the administration of a therapeutically effective amount of a compound selected within the compounds of formulae (I), (A), (B), (A1), (A2), (B1), (B2), (I*), (A*), (B*), (A1*), (A2*), (B1*) and (B2*) according to the invention, or of a pharmaceutical composition according to the invention or of a kit according to the invention to a patient in need thereof. Preferably, the bacteria are chosen amongst gram-positive bacteria or gram-negative bacteria, more preferably gram-negative bacteria.

The term "patient" means a person or an animal at risk of being infected by bacteria or, a person or an animal being infected by bacteria, preferably by gram-positive and by gram-negative bacteria, more preferably by gram-negative bacteria. As used herein, the term "patient" refers to a warm-blooded person or animal such as a mammal, preferably a human or a human child, who is afflicted with, or has the potential to be afflicted with one or more infections and conditions described herein. The identification of those subjects who are in need of treatment of herein-described diseases and conditions is well within the ability and knowledge of one skilled in the art. A veterinarian or a physician skilled in the art can readily identify, by the use of clinical tests, physical examination, medical or family history or biological and diagnostic tests, those subjects who are in need of such a treatment.

The expression "therapeutically effective amount" or "pharmaceutically effective amount" as used herein, refer to an amount of a compound according to the invention, which when administered to a patient in need thereof, is sufficient to effect treatment for disease-states, conditions, or disorders for which the compound has utility. Such an amount would be sufficient to elicit the biological or medical response of a tissue system, or patient that is sought by a researcher or a clinician. The amount of a compound according to the invention which constitutes a "therapeutically effective amount" will vary, notably depending on the compound itself and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a "therapeutically effective amount" can be determined by one of ordinary skilled in the art having regard to its own knowledge, and this disclosure. Preferably, the compound according to the invention is administered in an amount comprised between 0.1 to 30 g per day.

The compound according to the invention may be provided in an aqueous physiological buffer solution for parenteral administration. The compound of the present invention is also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described herein. The compound provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The pharmaceutical composition may be conveniently administered in unit dosage form and may be prepared by any method well-known in the pharmaceutical art, for example, as described in *Remington: The Science and Practice of Pharmacy*, 20th ed.; Gennaro, A. R., Ed.; Lippincott Williams & Wilkins: Philadelphia, Pa., 2000.

Preferred formulations include pharmaceutical compositions wherein a compound according to the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate or talc in any combination.

Liquid preparations for parenteral administration include sterile aqueous or non-aqueous solutions, suspensions and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compound. Intravenous vehicles can include fluid and nutrient replenishers, electrolyte replenishers, such as those based on Ringer's dextrose, and the like. Other potentially useful parenteral delivery systems for the active compound include ethylene-vinyl acetate copolymer particles, osmotic pumps, implantable infusion systems and liposomes.

Alternative modes of administration include formulations for inhalation, which include such means as dry powder, aerosol, or drops. They may be aqueous solutions comprising, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations.

Formulations suitable for transdermal administration can be presented as discrete patches and can be lipophilic emulsions or buffered, aqueous solutions, dissolved and/or dispersed in a polymer or an adhesive.

The invention is further illustrated but not restricted by the description of the following examples.

EXAMPLES

The following examples are provided for the purpose of illustrating the present invention and by no means should be interpreted to limit the scope of the present invention.

The first part represents the preparation of the compounds (intermediates and final compounds) whereas the second part describes the evaluation of antibacterial activity of compounds according to the invention.

Preparation of the Compounds and Biological Activity:
Abbreviations or symbols used herein include:
ACHN: 1,1'-azobis(cyclohexanecarbonitrile)
ACN: acetonitrile
AcOH: acetic acid
Bn: benzyl
Boc: tert-butoxycarbonyl
Boc$_2$O: tert-butoxycarbonyl anhydride
BocON: [2-(tert-butoxycarbonyloxyimino)-2-phenylacetonitrile]
bs: broad singlet
Burgess reagent: methyl N-(triethylammoniosulfonyl)carbamate
CFU: colony-forming units
CLSI: clinical laboratory standards institute
d: doublet
DBU: 1,8-diazabicyclo[5.4.0]undec-7-ene
DCM: dichloromethane
dd: doublet of doublet
ddd: doublet of doublet of doublet
ddt: doublet of doublet of triplet
dq: doublet of quartet
dt: doublet of triplet
DTA: di-tert-butylazodicarboxylate
DEAD: diethyl azodicarboxylate
Dess-Martin periodinane: 1,1,1-tris(acetyloxy)-1,1-dihydro-1,2-benziodoxol-3-(1H)-one
DIAD: diisopropyl azodicarboxylate
DIPEA: N,N-diisopropylethylamine
DMAP: 4-dimethylaminopyridine
DMF: N,N-dimethylformamide
DMSO: dimethylsulfoxide
EtOAc: ethyl acetate
Et$_2$O: diethyl ether
h: hoursHATU
HATU: 1-[Bis(dimethylamino)methylene]-1H-1,2,3-triazolo[4,5-b]pyridinium-3-oxid hexafluorophosphate
HOBt: 1-Hydroxybenzotriazole
m: multiplet
min: minutes
MeOH: methanol
MeONa: sodium methoxide
MIC: minimum inhibitory concentration MS: mass spectrometry
Ms: methanesulfonyl
MsCl: methanesulfonyl chloride
NBS: N-bromosuccinimide
NMR: nuclear magnetic resonance spectroscopy
Ns: nosyl, nitrobenzenesulfonyl
Pd(Ph$_3$)$_4$: tetrakis(triphenylphosphine)palladium(0)
PG: protective group
PhSH: thiophenol
PMe$_3$: trimethylphosphine
PPh$_3$: triphenylphosphine
Ppm: parts per million
q: quartet
rt: room temperature
s: singlet
SEM: [2-(trimethylsilyl)ethoxy]methyl
t: triplet
td: triplet of doublet
TBAF: tetra-n-butylammonium fluoride
TBDMS: tert-butyldimethylsilyl
TBDMSOTf: trifluoromethanesulfonic acid tert-butyldimethylsilyl ester
TBSOTf: trimethylsilyl trifluoromethanesulfonate
tBuOK: potassium tert-butoxide
TEA: trimethylamine
TFA: trifluoroacetic acid
THF: tetrahydrofuran
THP: tetrahydropyranyl
TLC: thin layer chromatography
TMSI: Iodotrimethylsilane
Tr: trityl (triphenylmethyl)

Example 1

Synthesis of sodium [(2S,5S)-2-methoxycarbonyl-4-[2-(methylamino)-2-oxo-ethoxy]imino-7-oxo-1,6-diazabicyclo[3.2.1]octan-6-yl] sulfate

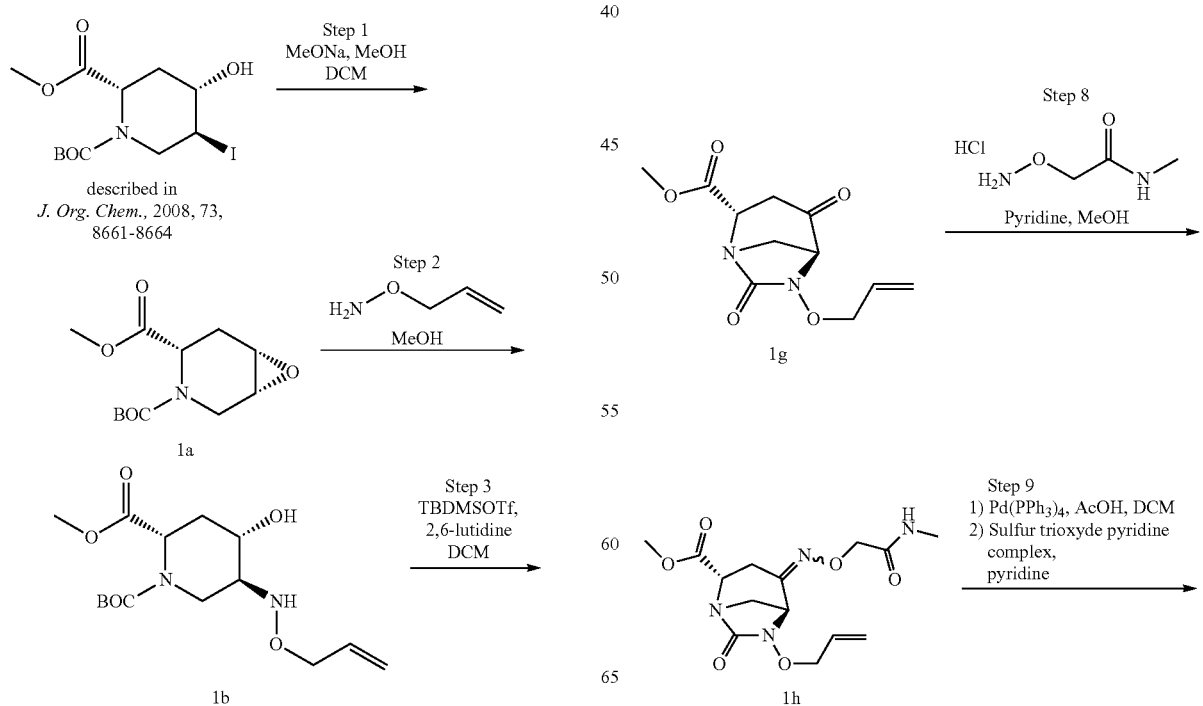

-continued

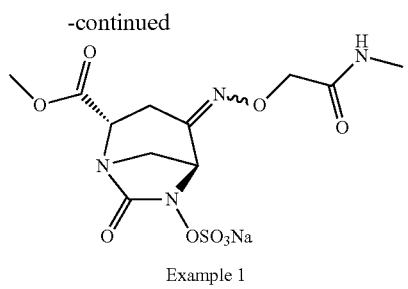

Example 1

Step 1: Preparation of intermediate 4-tert-butyl ester 3-methyl ester (1R,4S,6S)-7-oxa-3-aza-bicyclo[4.1.0]heptane-3,4-dicarboxylate (1a)

To a solution of 1-tert-butyl ester 2-methyl ester (2S,4S,5S)-4-hydroxy-5-iodo-piperidine-1,2-dicarboxylate (prepared according to the procedure described in *J. Org. Chem.*, 2008, 73, 8661-8664) (8.82 g, 22.90 mmol) in anhydrous DCM (100 mL) under inert atmosphere was added a MeONa solution 0.5 M in MeOH (45.81 mL, 22.90 mmol). The reaction mixture was stirred 20 h at rt, then the solution was washed with NaOH 1N. The organic layer was dried over $Na_2SO_4$, filtered and evaporated in vacuo. The crude residue was solubilized in mixture of EtOAc/cyclohexane (50/50) and filtered on silica gel cake to provide 4-tert-butyl ester 3-methyl ester (1R,4S,6S)-7-oxa-3-aza-bicyclo[4.1.0]heptane-3,4-dicarboxylate (1a) (5.33 g, 20.71 mmol, 90%) as a yellow oil.

MS m/z ($[M+Na]^+$) 280.

$^1$H NMR (400 MHz, $CDCl_3$): δ (ppm) 1.42 and 1.47 (2s, 9H), 2.18-2.26 (m, 1H), 2.85 (ddt, J=13.4/11.0/2.4 Hz, 1H), 3.31-3.17 (m, 2H), 3.68-3.81 (m, 4H), 3.88-3.94 (m, 1H), 4.53 and 4.73 (2dd, J=6.3/2.0 Hz, 1H).

Step 2: Preparation of intermediate 1-tert-butyl ester 2-methyl ester (2S,4S,5S)-5-allyloxyamino-4-hydroxy-piperidine-1,2-dicarboxylate (1b)

To a solution of 4-tert-butyl ester 3-methyl ester (1R,4S,6S)-7-oxa-3-aza-bicyclo[4.1.0]heptane-3,4-dicarboxylate (1a) (3.88 g, 15.09 mmol) in anhydrous MeOH (30 mL) under inert atmosphere was added O-allylhydroxylamine (5.51 g, 75.45 mmol). The reactor was sealed and the reaction was stirred 3 days at 80° C. MeOH was evaporated and the residue was purified by flash chromatography on silica gel (heptane/EtOAc 80/20 to 0/100) to provide 1-tert-butyl ester 2-methyl ester (2S,4S,5S)-5-allyloxyamino-4-hydroxy-piperidine-1,2-dicarboxylate (1b) (3.12 g, 9.44 mmol, 62%) as a colorless oil.

MS m/z ($[M+H]^+$) 331.

$^1$H NMR (400 MHz, $CDCl_3$): δ (ppm) 1.45 (s, 9H), 1.94-1.98 (m, 1H), 2.21-2.28 (m, 2H), 3.10 (bs, 1H), 3.47 (d, J=14.2 Hz, 1H), 3.73 (s, 3H), 3.90 (dd, J=14.2/2.6 Hz, 1H), 3.98-4.02 (m, 1H), 4.18 (dq, J=5.9/1.3 Hz, 2H), 4.72 (bs, 1H), 5.12-5.35 (m, 2H), 5.53 (s, 1H), 5.91 (ddt, J=17.3/10.3/5.9 Hz, 1H).

Step 3: Preparation of intermediate 1-tert-butyl ester 2-methyl ester (2S,4S,5S)-5-allyloxyamino-4-(tert-butyl-dimethyl-silanyloxy)-piperidine-1,2-dicarboxylate (1c)

To a solution of 1-tert-butyl ester 2-methyl ester (2S,4S,5S)-5-allyloxyamino-4-hydroxy-piperidine-1,2-dicarboxylate (1b) (3.95 g, 11.97 mmol) in anhydrous DCM (50 mL) under inert atmosphere at 0° C. was added 2,6-lutidine (1.67 mL, 14.36 mmol) followed by TBDMSOTf (2.88 mL, 12.58 mmol). The mixture was stirred for 3 h at 20° C. and then the solution was extracted with DCM, washed with saturated sodium hydrogenocarbonate aqueous solution. The organic phase was dried over $Na_2SO_4$, filtered and evaporated.

The product was purified by flash chromatography on silica gel (cyclohexane/EtOAc 90/10) to afford 1-tert-butyl ester 2-methyl ester (2S,4S,5S)-5-allyloxyamino-4-(tert-butyl-dimethyl-silanyloxy)-piperidine-1,2-dicarboxylate (1c) (4.55 g, 10.23 mmol, 85%) as a colorless oil.

MS m/z ($[M+H]^+$) 445.

$^1$H NMR (300 MHz, $CDCl_3$): δ (ppm) 0.04 (2s, 6H), 0.86 (s, 9H), 1.46 (bs, 9H), 2.00-2.24 (m, 2H), 2.90-3.20 (m, 1H), 3.36-3.55 (m, 1H), 3.70 (s, 3H), 3.83-4.05 (m, 2H), 4.09-4.26 (m, 2H), 4.54-4.73 (2bs, 1H), 5.04-5.42 (m, 2H), 5.50 (bs, 1H), 5.91 (ddt, J=17.3/10.4/5.9 Hz, 1H).

Step 4: Preparation of intermediate methyl (2S,4S,5S)-5-(allyloxyamino)-4-[tert-butyl(dimethyl)silyl]oxy-piperidine-2-carboxylate (1d)

To a solution of 1-tert-butyl ester 2-methyl ester (2S,4S,5S)-5-allyloxyamino-4-(tert-butyl-dimethyl-silanyloxy)-piperidine-1,2-dicarboxylate (1c) (0.368 g, 0.83 mmol) in anhydrous DCM (16 mL) under inert atmosphere at rt, was added slowly TMST (177 μL, 1.24 mmol). The reaction mixture was stirred for 30 min at rt. The mixture was then quenched at 0° C. with MeOH (1 mL). The mixture was evaporated under vacuum and the resulting residue was purified by flash chromatography on silica gel (DCM/MeOH 97/3) to provide methyl (2S,4S,5S)-5-(allyloxyamino)-4-[tert-butyl(dimethyl)silyl]oxy-piperidine-2-carboxylate (1d) (0.325 g, 0.829 mmol, quantitative yield) as a yellow solid.

MS m/z ($[M+H]^+$) 345.

$^1$H NMR (400 MHz, $CDCl_3$): δ (ppm) 0.09 (2s, 6H), 0.88 (s, 9H), 2.15 (dt, J=15.0/8.1 Hz, 1H), 2.46 (dt, J=14.2/4.3 Hz, 1H), 3.20-3.32 (m, 2H), 3.79 (dd, J=12.3, 3.0 Hz, 1H), 3.84 (s, 4H), 3.95-4.03 (m, 1H), 4.10-4.26 (m, 3H), 5.18-5.36 (m, 2H), 5.91 (ddt, J=16.6/10.4/6.0 Hz, 1H).

Step 5: Preparation of intermediate methyl (2S,4S,5S)-6-allyloxy-4-[tert-butyl(dimethyl)silyl] oxy-7-oxo-1,6-diazabicyclo[3.2.1]octane-2-carboxylate (1e)

To a solution of (2S,4S,5S)-5-(allyloxyamino)-4-[tert-butyl(dimethyl)silyl]oxy-piperidine-2-carboxylate (1d) (0.325 g, 0.829 mmol) and 4-picoline (322 μL, 3.31 mmol) in anhydrous DCM (16 mL) at 0° C. was added diphosgene (55 μL, 0.45 mmol) as a solution in DCM (4 mL, flow=0.25 mL/min). Once addition was complete, the reaction was stirred to rt overnight. The mixture was washed with a saturated sodium hydrogenocarbonate aqueous solution then water, dried over $Na_2SO_4$, filtered and concentrated. The crude residue was purified by flash chromatography on silica gel (cyclohexane/EtOAc 90/10) to provide intermediate methyl (2S,4S,5S)-6-allyloxy-4-[tert-butyl(dimethyl)silyl]oxy-7-oxo-1,6-diazabicyclo[3.2.1]octane-2-carboxylate (1e) (0.176 g, 0.47 mmol, 57% over 2 steps).

MS m/z ($[M+H]^+$) 371.

$^1$H NMR (300 MHz, $CDCl_3$): δ (ppm) 0.05 (2s, 6H), 0.86 (s, 9H), 2.21 (d, J=15.8 Hz, 1H), 2.37 (ddd, J=15.7/8.7/4.5 Hz, 1H), 2.99-3.08 (m, 1H), 3.52 (t, J=3.7 Hz, 1H), 3.70 (d, J=12.1 Hz, 1H), 3.77 (s, 3H), 4.05 (d, J=8.5 Hz, 1H), 4.23-4.27 (m, 1H), 4.38-4.54 (m, 2H), 5.27-5.43 (m, 2H), 6.02 (ddt, J=16.9/10.3/6.4 Hz, 1H).

Step 6: Preparation of intermediate methyl (2S,4S,5S)-6-allyloxy-4-hydroxy-7-oxo-1,6-diazabicyclo[3.2.1]octane-2-carboxylate (1f)

To a solution of methyl (2S,4S,5S)-6-allyloxy-4-[tert-butyl(dimethyl)silyl] oxy-7-oxo-1,6-diazabicyclo[3.2.1]octane-2-carboxylate (1e) (0.722 g, 1.95 mmol) in anhydrous ACN (20 mL) under inert atmosphere was added dropwise TEA.3HF (320 µL, 1.95 mmol). The reaction mixture was stirred to 60° C. for 18 h. The mixture was diluted with EtOAc, washed with water, dried over $Na_2SO_4$, filtered and concentrated. The crude was purified by flash chromatography on silica gel (cyclohexane/EtOAc 50/50 to 0/100) to provide methyl (2S,4S,5S)-6-allyloxy-4-hydroxy-7-oxo-1,6-diazabicyclo[3.2.1]octane-2-carboxylate (1f) (0.361 g, 1.40 mmol, 72%) as a white solid.

MS m/z ([M+H]$^+$) 257.

$^1$H NMR (400 MHz, CDCl$_3$): δ (ppm) 2.13 (dd, J=16.3/2.0 Hz, 1H), 2.33 (ddd, J=16.2/8.0/5.1 Hz, 1H), 2.95-3.04 (m, 1H), 3.36-3.45 (m, 2H), 3.67-3.76 (m, 1H), 3.80 (s, 3H), 4.08 (d, J=7.9 Hz, 1H), 4.29 (q, J=4.7 Hz, 1H), 4.31-4.51 (m, 2H), 5.23-5.39 (m, 2H), 5.98 (ddt, J=16.9/10.3/6.4 Hz, 1H).

Step 7: Preparation of intermediate methyl (2S,5S)-6-allyloxy-4,7-dioxo-1,6-diazabicyclo[3.2.1]octane-2-carboxylate (1g)

To a solution of methyl (2S,4S,5S)-6-allyloxy-4-hydroxy-7-oxo-1,6-diazabicyclo[3.2.1]octane-2-carboxylate (1f) (0.361 g, 1.41 mmol) in anhydrous DCM (30 mL) under inert atmosphere at 0° C. was added the reagent Dess-Martin periodinane (0.847 g, 1.41 mmol). The reaction was stirred for 18 h at rt, then the mixture was washed with a saturated sodium hydrogenocarbonate aqueous solution, a 15% sodium thiosulfate solution, water, dried oved $Na_2SO_4$, filtered and concentrated under vacuum. The residue was purified by flash chromatography on silica gel (cyclohexane/EtOAc 80/20 to 0/100) to afford intermediate methyl (2S,5S)-6-allyloxy-4,7-dioxo-1,6-diazabicyclo[3.2.1]octane-2-carboxylate (1g) (0.333 g, 1.31 mmol, 92%) as a colorless oil.

MS m/z ([M+H]$^+$) 255.

$^1$H NMR (400 MHz, CDCl$_3$): δ (ppm) 2.91-3.05 (m, 2H), 3.31 (d, J=12.9 Hz, 1H), 3.56-3.66 (m, 1H), 3.79 (s, 3H), 3.99 (d, J=3.8 Hz, 1H), 4.35-4.50 (m, 2H), 4.53 (ddd, J=6.3/4.8/1.5 Hz, 1H), 5.28-5.41 (m, 2H), 5.89-6.04 (m, 1H).

Step 8: Preparation of intermediate methyl (2S,5S)-6-allyloxy-4-[2-(methylamino)-2-oxo-ethoxy]imino-7-oxo-1,6-diazabicyclo[3.2.1]octane-2-carboxylate (1h)

To a solution of methyl (2S,5S)-6-allyloxy-4,7-dioxo-1,6-diazabicyclo[3.2.1]octane-2-carboxylate (1g) (0.140 g, 0.55 mmol) in anhydrous MeOH (5.5 mL) under inert atmosphere was added successively pyridine (93 µL, 1.16 mmol) and 2-aminooxy-N-methyl-acetamide.HCl (0.081 g, 0.58 mmol). The reaction mixture was stirred for 2h30 at rt. The reaction mixture was concentrated under vacuum and the residue was purified by flash chromatography on silica gel (DCM/MeOH 100/0 to 98/2) to provide intermediate methyl (2S,5S)-6-allyloxy-4-[2-(methylamino)-2-oxo-ethoxy]imino-7-oxo-1,6-diazabicyclo[3.2.1] octane-2-carboxylate (1h) (0.153 g, 0.45 mmol, ratio Z/E: 50/50, 81%).

MS m/z ([M+H]$^+$) 341.

$^1$H NMR (400 MHz, CDCl$_3$): δ (ppm) 2.58-2.98 (m, 4.5H), 3.05 (d, J=12.3 Hz, 0.5H), 3.17 (d, J=12.5 Hz, 0.5H), 3.37-3.47 (m, 1.5H), 3.76 (2s, 3H), 4.14 (d, J=3.5 Hz, 0.5H), 4.25-4.59 (m, 5H), 5.04 (d, J=3.3 Hz, 0.5H), 5.24-5.40 (m, 2H), 5.86-6.03 (m, 1H), 6.32 (2bs, 1H).

Step 9: Preparation of sodium [(2S,5S)-2-methoxycarbonyl-4-[2-(methylamino)-2-oxo-ethoxy]imino-7-oxo-1,6-diazabicyclo[3.2.1]octan-6-yl] sulfate (example 1)

To a solution of compound methyl (2S,5S)-6-allyloxy-4-[2-(methylamino)-2-oxo-ethoxy]imino-7-oxo-1,6-diazabicyclo[3.2.1]octane-2-carboxylate (1h) (0.100 g, 0.29 mmol) and glacial AcOH (35 µL, 0.59 mmol) in anhydrous DCM (4.5 mL) was added in one portion Pd(Ph$_3$)$_4$ (0.170 g, 0.15 mmol). After stirring for 1 h at rt, dry pyridine (2.75 mL) and sulfur trioxide pyridine complex (0.234 g, 1.47 mmol) were added to the mixture and the resulting solution was protected from light and stirred overnight at rt until the sulfatation was completed. The reaction mixture was concentrated under vacuum, diluted with DCM and filtered. The filtrate was concentrated and purified on silica gel (DCM/acetone 100/0 to 0/100) to provide 102 mg of a colorless oil of triphenyl-(propenyl)-phosphonium [(2S,5S)-2-methoxycarbonyl-4-[2-(methylamino)-2-oxo-ethoxy]imino-7-oxo-1,6-diazabicyclo[3.2.1]octan-6-yl] sulfate.

This oil was solubilized in a minimal volume of water and applied on a Dowex sodium form column (Dowex® 50WX8 hydrogen form stored with an aqueous solution of 2N NaOH and washed until neutral pH with water). The fractions containing the desired compound were combined, frozen and lyophilized to afford compound [(2S,5S)-2-methoxycarbonyl-4-[2-(methylamino)-2-oxo-ethoxy]imino-7-oxo-1,6-diazabicyclo[3.2.1]octan-6-yl] sulfate sodium salt (example 1) (0.053 g, 0.131 mmol, ratio Z/E: 50/50, 44% over 2 steps).

MS m/z ([M+H]$^+$) 381.

MS m/z ([M−H]$^−$) 379.

$^1$H NMR (300 MHz, D$_2$O): δ (ppm) 2.81 (2s, 3H), 2.93-3.18 (m, 2H), 3.37 (d, J=16.5 Hz, 0.5H), 3.39 (d, J=16.9 Hz, 0.5H), 3.57 (dd, J=19.6/2.4 Hz, 0.5H), 3.64-3.81 (m, 1H), 3.85 (2s, 3H), 4.49-4.67 (m, 3H), 5.55 (d, J=3.4 Hz, 0.5H)

Example 2

Synthesis of sodium (2S,5S)-6-hydroxy-4-[2-(methylamino)-2-oxo-ethoxy]imino-7-oxo-1,6-diazabicyclo[3.2.1]octane-2-carboxamide sulfate

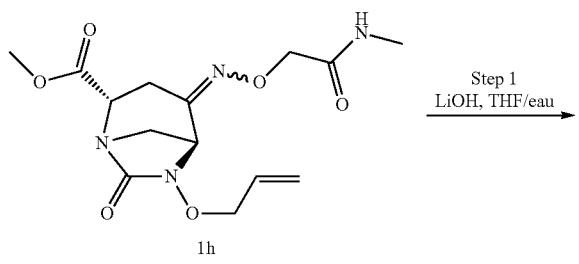

Step 1
LiOH, THF/eau

1h

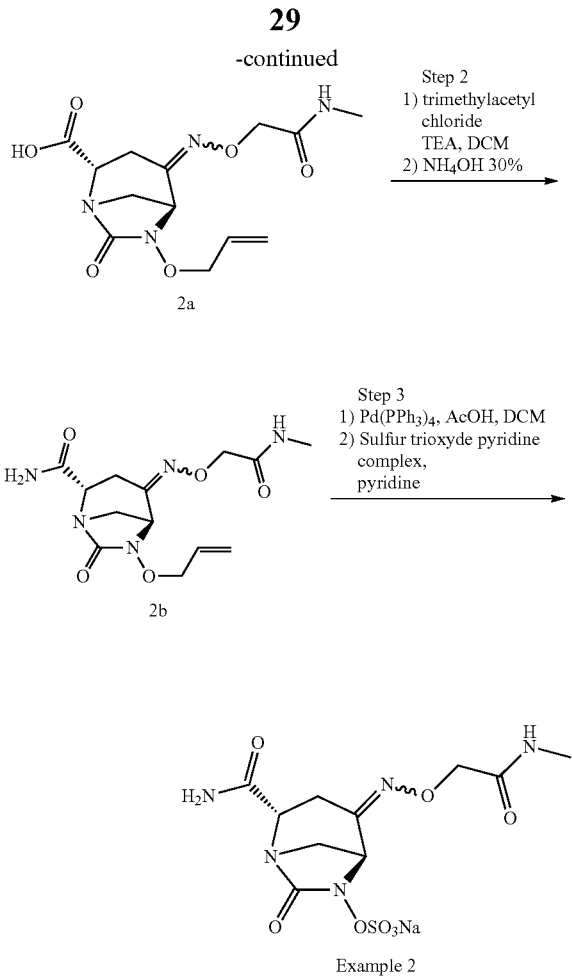

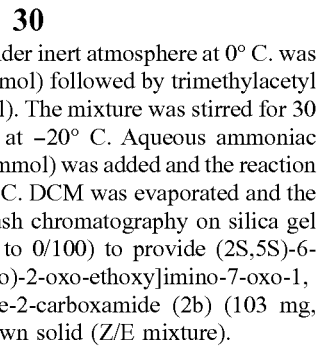

Example 2

Step 1: Preparation of intermediate (2S,5S)-6-allyloxy-4-[2-(methylamino)-2-oxo-ethoxy]imino-7-oxo-1,6-diazabicyclo[3.2.1]octane-2-carboxylic acid (2a)

To a solution of compound methyl (2S,5S)-6-allyloxy-4-[2-(methylamino)-2-oxo-ethoxy]imino-7-oxo-1,6-diazabicyclo[3.2.1]octane-2-carboxylate (1h) (0.310 g, 0.91 mmol) in a mixture of THF (4.8 mL) and water (2.4 mL) was added LiOH (21 mg, 0.91 mmol). The reaction mixture was stirred for 6 h at rt. The mixture was extracted with EtOAc (3×5 mL). The aqueous layer was acidified to pH=1 with a solution of HCl 2N and extracted with EtOAc (5×10 mL). The organic phase was dried over sodium sulfate, filtered and evaporated to afford (2S,5S)-6-allyloxy-4-[2-(methylamino)-2-oxo-ethoxy]imino-7-oxo-1,6-diazabicyclo[3.2.1]octane-2-carboxylic acid (2a) (135 mg, 0.41 mmol, 45%) as a white solid (Z/E mixture).

MS m/z ([M+H]$^+$) 327.
MS m/z ([M−H]$^−$) 325.

Step 2: Preparation of intermediate (2S,5S)-6-allyloxy-4-[2-(methylamino)-2-oxo-ethoxy]imino-7-oxo-1,6-diazabicyclo[3.2.1]octane-2-carboxamide (2b)

To a solution of compound (2S,5S)-6-allyloxy-4-[2-(methylamino)-2-oxo-ethoxy]imino-7-oxo-1,6-diazabicyclo[3.2.1]octane-2-carboxylic acid (2a) (135 mg, 0.41 mmol) in anhydrous DCM (4 mL) under inert atmosphere at 0° C. was added TEA (70 μL, 0.50 mmol) followed by trimethylacetyl chloride (53 μL, 0.43 mmol). The mixture was stirred for 30 min at 0° C. then cooled at −20° C. Aqueous ammoniac solution 30% (69 μL, 1.65 mmol) was added and the reaction was stirred for 1 h at −20° C. DCM was evaporated and the residue was purified by flash chromatography on silica gel (DCM/propan-2-ol: 100/0 to 0/100) to provide (2S,5S)-6-allyloxy-4-[2-(methylamino)-2-oxo-ethoxy]imino-7-oxo-1,6-diazabicyclo[3.2.1]octane-2-carboxamide (2b) (103 mg, 0.32 mmol, 76%) as a brown solid (Z/E mixture).

MS m/z ([M+H]$^+$) 326.
MS m/z ([M−H]$^−$) 324.

$^1$H NMR (400 MHz, CDCl$_3$): δ (ppm) 2.55 (ddd, J=18.4/9.3/2.2 Hz, 0.6H), 2.76-2.89 (m, 3H), 2.98 (t, J=12.4 Hz, 1H), 3.19 (dd, J=17.8/5.0 Hz, 0.4H), 3.38-3.51 (m, 1H), 3.77-3.88 (m, 1H), 4.13-4.25 (m, 2H), 4.35-4.73 (m, 4.6H), 4.99-5.14 (m, 0.4H), 5.25-5.47 (m, 2H), 5.50-6.26 (m, 1H), 6.28-6.78 (m, 2H).

Step 3: Preparation of sodium [(2S,5S)-2-carbamoyl-4-[2-(methylamino)-2-oxo-ethoxy]imino-7-oxo-1,6-diazabicyclo[3.2.1]octan-6-yl] sulfate (example 2)

To a solution of compound (2S,5S)-6-allyloxy-4-[2-(methylamino)-2-oxo-ethoxy]imino-7-oxo-1,6-diazabicyclo[3.2.1]octane-2-carboxamide (2b) (103 mg, 0.32 mmol) and glacial AcOH (36 μL, 0.63 mmol) in anhydrous DCM (3.2 mL) was added in one portion Pd(PPh$_3$)$_4$ (0.183 g, 0.16 mmol). After stirring for 1 h at rt, dry pyridine (3.17 mL) and sulfur trioxide pyridine complex (0.252 g, 1.58 mmol) were added to the mixture and the resulting solution was protected from light and stirred overnight at rt until the sulfatation was completed. The reaction mixture was concentrated under vacuum, diluted with DCM and filtered. The filtrate was concentrated and purified on silica gel (propan-2-ol) to provide 65 mg of an orange oil of triphenyl-(propenyl)-phosphonium (2S,5S)-6-hydroxy-4-[2-(methylamino)-2-oxo-ethoxy]imino-7-oxo-1,6-diazabicyclo[3.2.1]octane-2-carboxamide sulfate.

This oil was solubilized in a minimal volume of water and applied on a Dowex sodium form column (Dowex® 50WX8 hydrogen form stored with an aqueous solution of 2N NaOH and washed until neutral pH with water). The fractions containing the desired compound were combined, frozen and lyophilized to afford 25 mg of impure [(2S,5S)-2-carbamoyl-4-[2-(methylamino)-2-oxo-ethoxy]imino-7-oxo-1,6-diazabicyclo[3.2.1]octan-6-yl] sulfate sodium salt, that was then purified by chromatography on reverse phase C-18 (water/ACN: 98/2). The fractions containing the desired compound were combined, frozen and lyophilized to afford sodium [(2S,5S)-2-carbamoyl-4-[2-(methylamino)-2-oxo-ethoxy]imino-7-oxo-1,6-diazabicyclo [3.2.1]octan-6-yl] sulfate (example 2) (6.8 mg, 0.017 mmol, ratio Z/E: 40/60, 5.5% over 2 steps) as a white solid.

MS m/z ([M−H]$^−$) 364.

$^1$H NMR (400 MHz, D$_2$O): δ (ppm) 2.80 (2s, 3H), 2.86-3.04 (m, 1H), 3.06-3.15 (m, 0.5H), 3.34 (dd, J=18.4/12.6 Hz, 1H), 3.54 (ddd, J=19.5/2.9/0.9 Hz, 0.5H), 3.64-3.86 (m, 1H), 4.31-4.40 (m, 1H), 4.54-4.64 (m, 2.6H), 5.50 (d, J=3.2 Hz, 0.4H).

Example 3

Synthesis of sodium [(2S, 5S)-4-(2-amino-2-oxo-ethoxy)imino-2-carbamoyl-7-oxo-1,6-diazabicyclo[3.2.1]octan-6-yl] sulfate

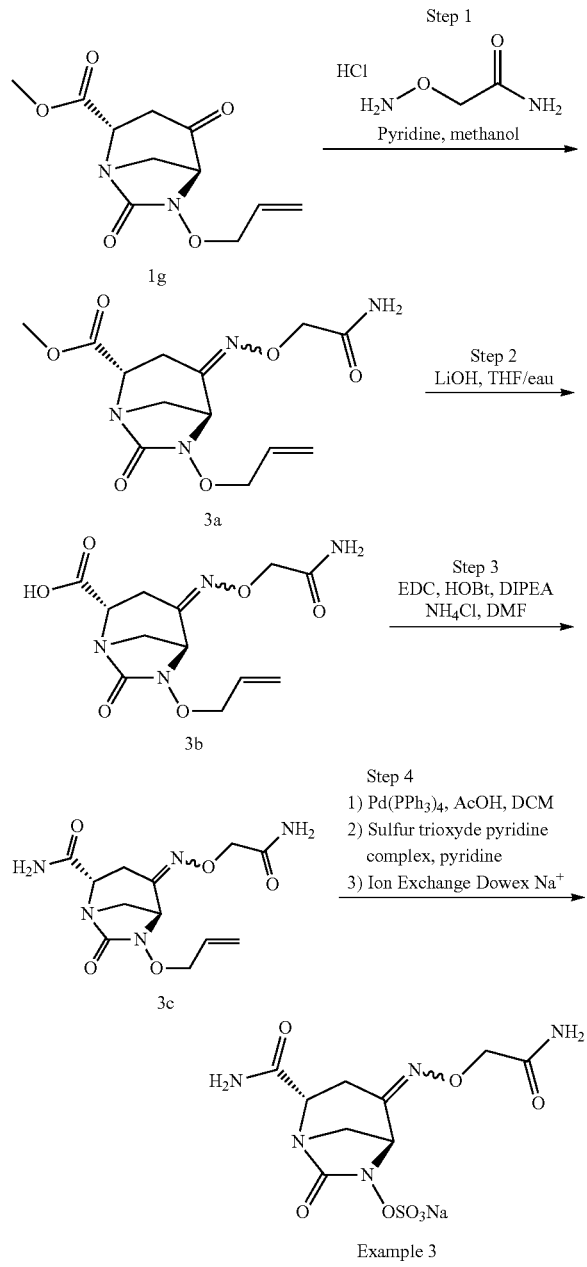

Step 1: Preparation of intermediate methyl (2S, 5S)-6-allyloxy-4-(2-amino-2-oxo-ethoxy)imino-7-oxo-1,6-diazabicyclo[3.2.1]octane-2-carboxylate (3a)

Using the procedure described in example 1 (step 8), methyl (2S,5S)-6-allyloxy-4,7-dioxo-1,6-diazabicyclo[3.2.1]octane-2-carboxylate (1g) (1.05 g, 4.13 mmol) is converted by reaction with the 2-(aminooxy)acetamide hydrochloride (0.495 g, 3.92 mmol) for 45 minutes into (2S, 5S)-6-allyloxy-4-(2-amino-2-oxo-ethoxy)imino-7-oxo-1,6-diazabicyclo[3.2.1]octane-2-carboxylate (3a) (1.14 g, 3.49 mmol, ratio Z/E 50/50, 85%) as a yellow oil after purification by flash chromatography (DCM/MeOH: 100/0 to 95/5).

MS m/z ([M+H]$^+$) 327.

$^1$H NMR (400 MHz, CDCl$_3$): δ (ppm) 2.73 (dd, J=18.5, 9.3 Hz, 0.5H), 2.85-3.00 (m, 1H), 3.10 (d, J=12.7 Hz, 0.5H), 3.23 (d, J=12.5 Hz, 0.5H), 3.40-3.55 (m, 1.5H), 3.81 (d, J=4.0 Hz, 3H), 4.20 (d, J=3.5 Hz, 0.5H), 4.31-4.67 (m, 5H), 5.08 (d, J=3.2 Hz, 0.5H), 5.31-5.45 (m, 2H), 5.52 (d, J=14.4 Hz, 1H), 5.92-6.07 (m, 1H), 6.31 (bs, 1H).

Step 2: Preparation of intermediate (2S, 5S)-6-allyloxy-4-(2-amino-2-oxo-ethoxy)imino-7-oxo-1,6-diazabicyclo[3.2.1]octane-2-carboxylic acid (3b)

To solution of (2S, 5S)-6-allyloxy-4-(2-amino-2-oxo-ethoxy)imino-7-oxo-1,6-diazabicyclo[3.2.1]octane-2-carboxylate (3a) (1.00 g, 3.06 mmol) in a mixture of acetone and water (2.38 mL/0.95 mL) to −10° C. was added slowly LiOH 1N (3.06 mL, 3.06 mmol). The reaction was stirring 5 min to −10° C. and the mixture was neutralised to pH =7 with HCl 1N. The solution was washed with DCM. Aqueous phase was frozen and lyophilized to provided 908 mg of a white solid. This solid was purified by flash chromatography on C18 (H$_2$O/ACN: 98/2) The fractions containing the desired compound were combined, frozen and lyophilized to afford (2S, 5S)-6-allyloxy-4-(2-amino-2-oxo-ethoxy)imino-7-oxo-1,6-diazabicyclo[3.2.1]octane-2-carboxylic acid (3b) (0.671 g, 2.14 mmol, 70%) as a Z/E 50/50 mixture.

MS m/z ([M+H]$^+$) 313.

$^1$H NMR (400 MHz, D$_2$O): δ (ppm) 2.77-2.90 (m, 1H), 3.04 (dd, J=17.1/3.2 Hz, 0.5H), 3.24 (dd, J=12.5/3.3 Hz, 1H), 3.48-3.65 (m, 1H), 4.06-4.13 (m, 1H), 4.43 (d, J=3.6 Hz, 0.5H), 4.53 (dd, J=14.2/6.6 Hz, 2H), 4.60 (s, 1H), 4.63 (s, 1H), 5.40-5.53 (m, 3H), 5.98-6.14 (m, 1H).

Step 3: Preparation of intermediate (2S, 5S)-6-allyloxy-4-(2-amino-2-oxo-ethoxy)imino-7-oxo-1,6-diazabicyclo[3.2.1]octane-2-carboxamide (3c)

To a solution of compound (2S, 5S)-6-allyloxy-4-(2-amino-2-oxo-ethoxy)imino-7-oxo-1,6-diazabicyclo[3.2.1]octane-2-carboxylic acid (3b) (0.360 g, 1.15 mmol) in anhydrous DMF (15 mL) was added HOBT (0.171 g, 1.27 mmol), DIPEA (0.42 mL, 2.41 mmol), ammonium chloride (0.123 g, 2.30 mmol), then EDAC (0.232 g, 1.21 mmol). After stirring for 16 h at rt, HOBT (0.083 g, 0.614 mmol), DIPEA (0.21 mL, 1.20 mmol), ammonium chloride (0.62 g, 1.15 mmol) and EDAC (0.115 g, 0.600 mmol) were added again to the mixture and the reaction was stirred 29 h at rt. The reaction mixture was concentrated under a flow of nitrogen. The product was purified by flash chromatography on silica gel (DCM/propan-2-ol: gradient 100/0 to 0/100) to afford (2S, 5S)-6-allyloxy-4-(2-amino-2-oxo-ethoxy)imino-7-oxo-1,6-diazabicyclo[3.2.1]octane-2-carboxamide (3c) (0.238 g, 0.764 mmol, 66%) as a white solid after precipitation in MeOH.

MS m/z ([M+H]$^+$) 312.

$^1$H NMR (400 MHz, MeOD): δ (ppm) 2.60-2.79 (m, 1H), 3.21-3.28 (m, 3H), 3.40-3.54 (m, 1H), 3.63-3.82 (m, 3H), 4.11-4.22 (m, 1H), 4.30 (d, J=3.6 Hz, 0.5H), 4.42-4.51 (m, 3H), 4.54 (s, 1H), 5.27 (d, J=3.5 Hz, 0.5H), 5.30-5.37 (m, 1H), 5.38-5.46 (m, 1H), 5.97-6.14 (m, 1H).

Step 4: Preparation of sodium [(2S, 5S)-4-(2-amino-2-oxo-ethoxy)imino-2-carbamoyl-7-oxo-1,6-diazabicyclo[3.2.1]octan-6-yl] sulfate (example 3)

To a solution of (2S, 5S)-6-allyloxy-4-(2-amino-2-oxo-ethoxy)imino-7-oxo-1,6-diazabicyclo[3.2.1]octane-2-carboxamide (3c) (0.100 g, 0.321 mmol) and glacial AcOH (0.072 mL, 1.28 mmol) in anhydrous DMF (5.35 mL) was added Pd(PPh$_3$)$_4$ (0.370 g, 0.320 mmol). After stirring for 48 h at rt, dry pyridine (3.20 mL) and sulfur trioxide pyridine complex (0.255 g, 1.60 mmol) were added to the mixture and the resulting solution was protected from light and stirred 16 h at rt then 26 h to 40° C. until the sulfatation was completed. The reaction mixture was concentrated under flow of nitrogen, diluted with DCM and filtered. The filtrate was concentrated and purified by flash chromatography on silica gel (DCM/acetone/propan-2-ol: gradient 100/0/0 to 0/100/0 to 0/0/100) to provide 40 mg of an orange oil of triphenyl-(propenyl)-phosphonium [(2S, 5S)-4-(2-amino-2-oxo-ethoxy)imino-2-carbamoyl-7-oxo-1,6-diazabicyclo[3.2.1]octan-6-yl] sulfate.

This oil was solubilized in a minimal volume of water and applied on a Dowex sodium form column (Dowex® 50WX8 hydrogen form stored with an aqueous solution of 2N NaOH and washed until neutral pH with water). The fractions containing the desired compound were combined, frozen and lyophilized to afford 12.5 mg of impure sodium (2S, 5S)-6-hydroxy-4-[2-(methylamino)-2-oxo-ethoxy]imino-7-oxo-1,6-diazabicyclo[3.2.1]octane-2-carboxamide sulfate. The mixture was purified by flash chromatography on C18 (H$_2$O/ACN: 98/2) The fractions containing the desired compound were combined, frozen and lyophilized to afford sodium [(2S, 5S)-4-(2-amino-2-oxo-ethoxy)imino-2-carbamoyl-7-oxo-1,6-diazabicyclo[3.2.1]octan-6-yl] sulfate (example 3) (1.30 mg, 0.003 mmol, ratio Z/E: 30/70, 1.0%) as a white solid.

MS m/z ([M–H]$^-$) 350.

$^1$H NMR (400 MHz, D$_2$O): δ (ppm) 2.85-3.03 (m, 1H), 3.10 (dd, J=17.5/5.4 Hz, 0.3H), 3.27-3.39 (m, 1H), 3.54 (dd, J=19.4/2.8 Hz, 0.7H), 3.63-3.79 (m, 1H), 4.31-4.40 (m, 1H), 4.55-4.70 (m, 2.7H), 5.49 (d, J=3.2 Hz, 0.3H).

Example 4

Synthesis of sodium and 2,2,2-trifluoroacetate [(2S, 5S)-4-(2-ammoniumethoxyimino)-2-carbamoyl-7-oxo-1,6-diazabicyclo[3.2.1]octan-6-yl] sulfate

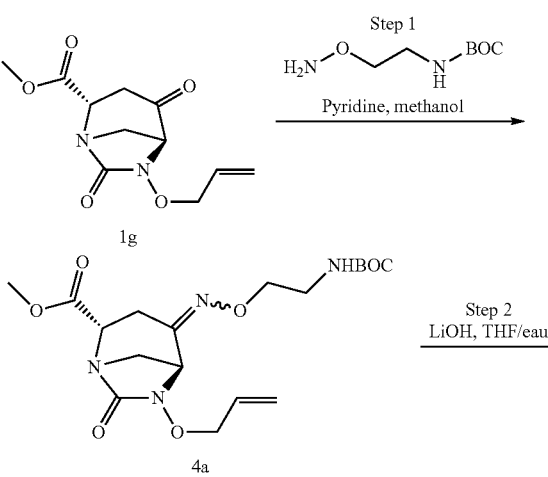

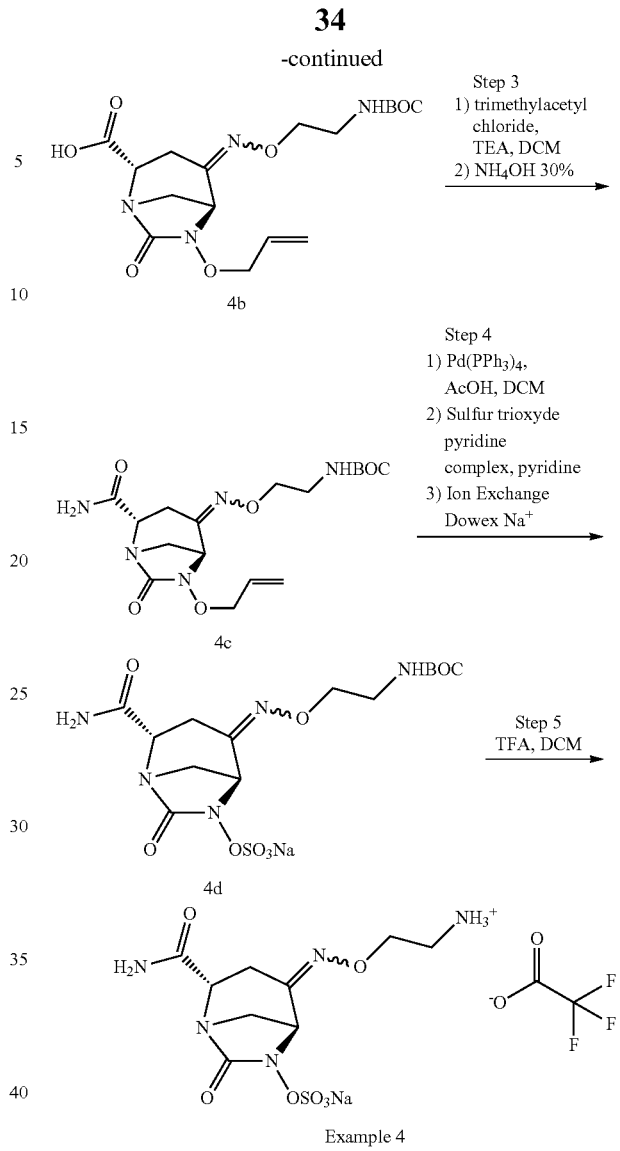

Example 4

Step 1: Preparation of intermediate methyl (2S, 5S)-6-allyloxy-4-[2-(tert-butoxycarbonylamino)ethoxyimino]-7-oxo-1,6-diazabicyclo[3.2.1]octane-2-carboxylate (4a)

Using the procedure described in example 1 (step 8), methyl (2S,5S)-6-allyloxy-4,7-dioxo-1,6-diazabicyclo[3.2.1]octane-2-carboxylate (1g) (0.862 g, 3.39 mmol) is converted by reaction with the tert-butyl N-(2-aminooxy-ethyl)carbamate (0.568 g, 3.22 mmol) for 27 h into methyl (2S, 5S)-6-allyloxy-4-[2-(tert-butoxycarbonylamino)ethoxyimino]-7-oxo-1,6-diazabicyclo[3.2.1]octane-2-carboxylate (4a) (0.370 g, 0.897 mmol, ratio Z/E 50/50, 26%) as a colorless oil after purification by flash chromatography on silica gel (heptane/EtOAc: 80/20 to 0/100).

MS m/z ([M+H-Boc]$^+$)/([M+H]$^+$) 313/413.

$^1$H NMR (300 MHz, CDCl$_3$): δ (ppm) 1.44 (2s, 9H), 2.73-3.03 (m, 1H), 3.16 (t, J=12.7 Hz, 1H), 3.29-3.56 (m, 3H), 3.80 (d, J=0.7 Hz, 3H), 4.05-4.19 (m, 3.5H), 4.31-4.54 (m, 3H), 4.83 (d, J=28.1 Hz, 1H), 5.08 (d, J=3.6 Hz, 0.5H), 5.27-5.45 (m, 2H), 5.91-6.11 (m, 1H).

Step 2: Preparation of intermediate (2S, 5S)-6-allyloxy-4-[2-(tert-butoxycarbonylamino) ethoxyimino]-7-oxo-1,6-diazabicyclo[3.2.1]octane-2-carboxylic acid (4b)

Using the procedure described in example 3 (step 2), the intermediate (methyl (2S, 5S)-6-allyloxy-4-[2-(tert-butoxycarbonylamino)ethoxyimino]-7-oxo-1,6-diazabicyclo[3.2.1]octane-2-carboxylate (4a) (0.590 g, 1.43 mmol) is converted into (2S, 5S)-6-allyloxy-4-[2-(tert-butoxycarbonylamino) ethoxyimino]-7-oxo-1,6-diazabicyclo[3.2.1]octane-2-carboxylic acid (4b) in mixture with (2S, 5S)-5-[allyloxy(methoxycarbonyl)amino]-4-[2-(tert-butoxycarbonylamino)ethoxyimino]piperidine-2-carboxylic acid (0.393 g) after purification by flash chromatography on silica gel (DCM/propan-2-ol : 80/20 to 0/100). The mixture is used without further purification.

MS m/z ([M+H-Boc]$^+$)/([M+H]$^+$) 299/399.

Step 3: Preparation of intermediate tert-butyl N-[2-[(2S,5S)-6-allyloxy-2-carbamoyl-7-oxo-1,6-diazabicyclo[3.2.1]octan-4-ylidene]amino]oxyethyl]carbamate (4c)

Using the procedure described in example 2 (step 2), the mixture of (2S, 5S)-6-allyloxy-4-[2-(tert-butoxycarbonylamino) ethoxyimino]-7-oxo-1,6-diazabicyclo[3.2.1]octane-2-carboxylic acid (4b) (0.300 g, 0.753 mmol) is converted into N-[2-[[(2S,5S)-6-allyloxy-2-carbamoyl-7-oxo-1,6-diazabicyclo[3.2.1]octan-4-ylidene]amino]oxyethyl] carbamate (4c) (0.202 g, 2.14 mmol, 35% over 2 steps) as a Z/E 50/50 mixture after purification by flash chromatography on silica gel (DCM/propan-2-ol : 100/0 to 0/100).

MS m/z ([M+H-Boc]$^+$)/([M+H]$^+$) 298/398.

$^1$H NMR (400 MHz, CDCl$_3$): δ (ppm) 1.41 (2s, 9H), 2.60-2.80 (m, 0.5H), 2.93 (t, J=12.0 Hz, 0.5H), 3.17-3.51 (m, 3H), 3.71 (d, J=19.0 Hz, 0.5H), 4.05-4.22 (m, 3H), 4.39-4.53 (m, 1.5H), 4.74-5.01 (m, 1H), 5.08 (d, J=3.6 Hz, 0.5H), 5.27-5.44 (m, 2H), 5.64 (bs, 3H), 5.86-6.08 (m, 1.5H), 6.70 (d, J=20.8 Hz, 1H)

Step 4: Preparation of sodium [(2S, 5S)-4-[2-(tert-butoxycarbonylamino)ethoxyimino]-2-carbamoyl-7-oxo-1,6-diazabicyclo[3.2.1]octan-6-yl] sulfate (4d)

Using the procedure described in example 3 (step 4), the intermediate N-[2-[[(2S,5S)-6-allyloxy-2-carbamoyl-7-oxo-1,6-diazabicyclo[3.2.1]octan-4-ylidene]amino]oxyethyl] carbamate (4c) (0.237 g, 0.596 mmol) provided 135 mg of triphenyl-(propenyl)-phosphonium [(2S, 5S)-4-[2-(tert-butoxycarbonylamino)ethoxyimino]-2-carbamoyl-7-oxo-1,6-diazabicyclo [3.2.1]octan-6-yl] sulfate after purification on silica gel (DCM/acetone/propan-2-ol: gradient 100/0/0 to 0/100/0 to 0/0/100). This oil was solubilized in a minimal volume of water and applied on a Dowex sodium form column (Dowex® 50WX8 hydrogen form stored with an aqueous solution of 2N NaOH and washed until neutral pH with water). The fractions containing the desired compound were combined, frozen and lyophilized to afford sodium [(2S, 5S)-4-[2-(tert-butoxycarbonylamino)ethoxyimino]-2-carbamoyl-7-oxo-1,6-diazabicyclo[3.2.1]octan-6-yl] sulfate (4d) (75 mg, 0.163 mmol, ratio Z/E: 40/60, 27%) as a white solid.

MS m/z ([M−H]$^−$) 436.

$^1$H NMR (400 MHz, D$_2$O): δ (ppm): 1.42 (s, 9H), 2.81-2.97 (m, 1H), 3.08 (dd, J=17.3, 5.0 Hz, 0.5H), 3.27 (d, J=12.6 Hz, 1H), 3.30-3.47 (m, 2.5H), 3.69 (ddd, J=37.9/12.7/3.6 Hz, 1H), 4.07-4.20 (m, 2H), 4.29-4.36 (m, 1H), 4.57 (d, J=3.4 Hz, 0.6H), 5.42 (d, J=3.3 Hz, 0.4H)

Step 5: Preparation of sodium and 2,2,2-trifluoroacetate [(2S, 5S)-4-(2-ammoniumethoxyimino)-2-carbamoyl-7-oxo-1,6-diazabicyclo[3.2.1]octan-6-yl] sulfate (example 4)

To a solution of TFA (2 mL, 26.13 mmol) in anhydrous DCM (2 mL) at 0° C., is added a suspension of sodium [(2S, 5S)-4-[2-(tert-butoxycarbonylamino)ethoxyimino]-2-carbamoyl-7-oxo-1,6-diazabicyclo[3.2.1]octan-6-yl] sulfate (4d) (75 mg, 0.163 mmol) in anhydrous DCM (1 mL). The mixture is stirred 20 min to 0° C. and concentrated. The residual oil is diluted in water (3 mL), frozen and lyophilized to afford sodium and 2,2,2-trifluoroacetate [(2S,5S)-4-(2-ammonium-ethoxyimino)-2-carbamoyl-7-oxo-1,6-diazabicyclo[3.2.1]octan-6-yl] sulfate (Example 4) (56.3 mg, 0.118 mmol, ratio Z/E: 40/60, 72%) as a yellow solid.

MS m/z ([M+H]$^+$) 338.

MS m/z ([M−H]$^−$) 336.

$^1$H NMR (300 MHz, D$_2$O): δ (ppm) 2.80-3.01 (m, 1H), 3.03-3.56 (m, 4H), 3.59-3.91 (m, 1H), 4.23-4.45 (m, 3H), 4.59 (d, J=3.4 Hz, 0.6H), 5.45 (d, J=3.2 Hz, 0.4H)

Example 5

Synthesis of sodium and 2,2,2-trifluroacetate [(2S, 5S)-4-(2-amino-2-oxo-ethoxy)imino-2-(azaniumylmethyl)-7-oxo-1,6-diazabicyclo[3.2.1]octan-6-yl] sulfate

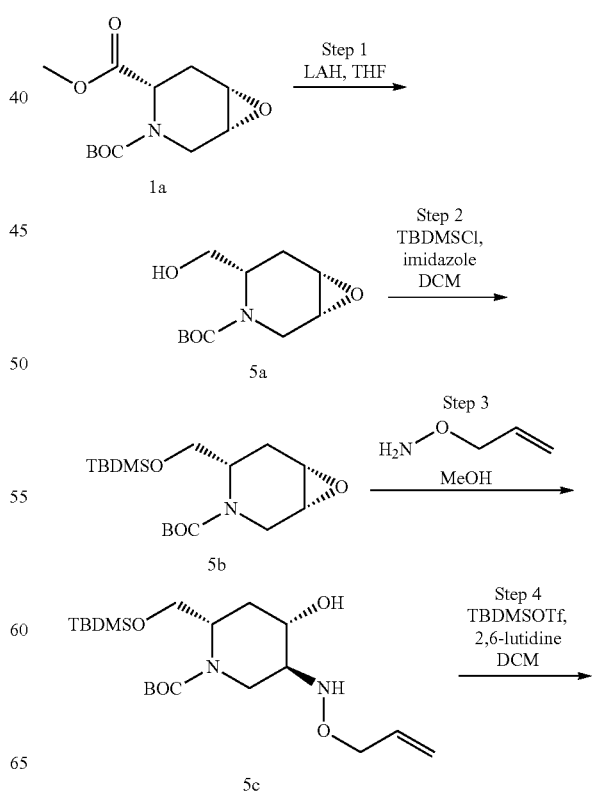

US 10,570,131 B2

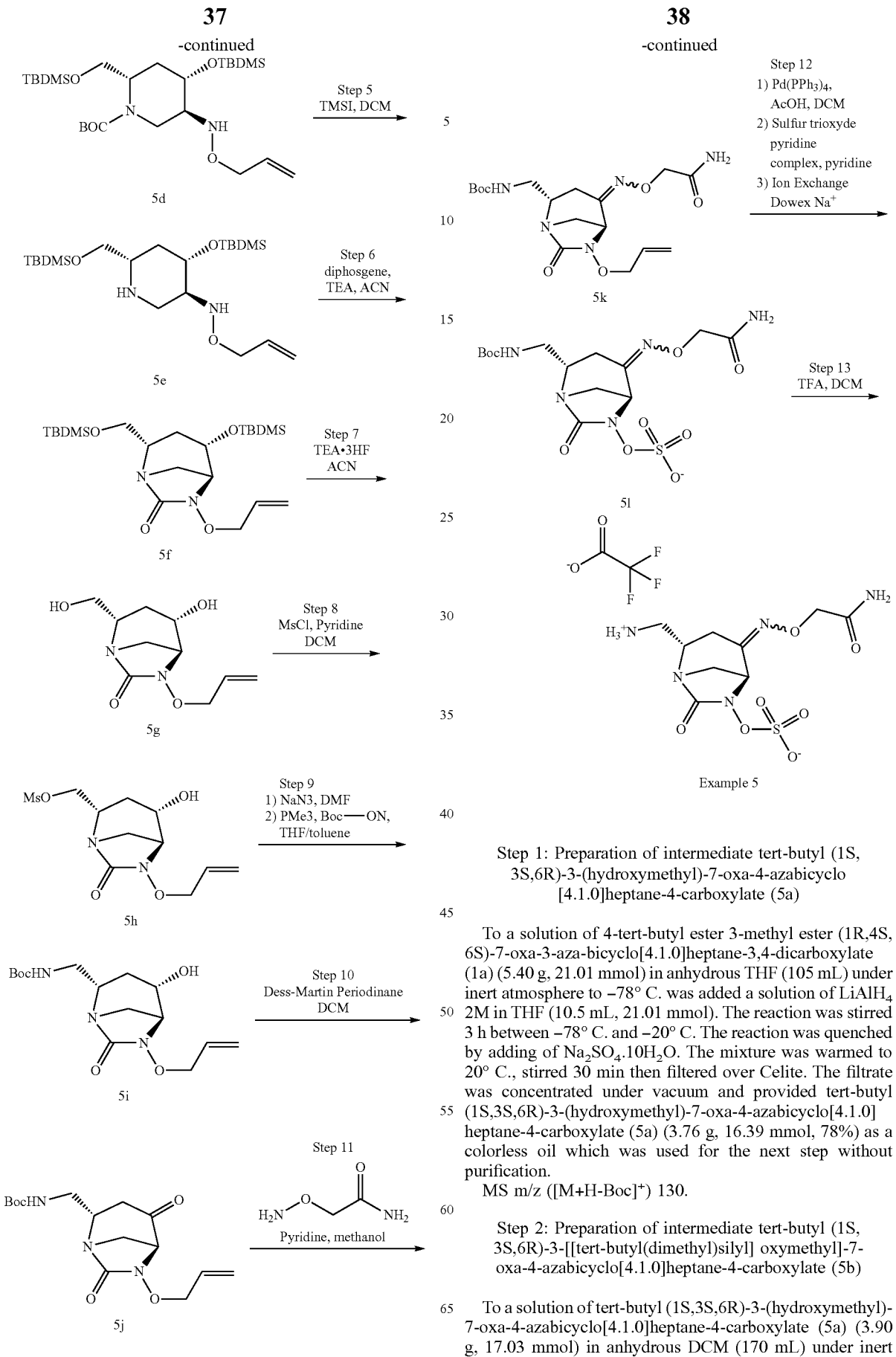

Step 1: Preparation of intermediate tert-butyl (1S, 3S,6R)-3-(hydroxymethyl)-7-oxa-4-azabicyclo [4.1.0]heptane-4-carboxylate (5a)

To a solution of 4-tert-butyl ester 3-methyl ester (1R,4S, 6S)-7-oxa-3-aza-bicyclo[4.1.0]heptane-3,4-dicarboxylate (1a) (5.40 g, 21.01 mmol) in anhydrous THF (105 mL) under inert atmosphere to −78° C. was added a solution of LiAlH$_4$ 2M in THF (10.5 mL, 21.01 mmol). The reaction was stirred 3 h between −78° C. and −20° C. The reaction was quenched by adding of Na$_2$SO$_4$.10H$_2$O. The mixture was warmed to 20° C., stirred 30 min then filtered over Celite. The filtrate was concentrated under vacuum and provided tert-butyl (1S,3S,6R)-3-(hydroxymethyl)-7-oxa-4-azabicyclo[4.1.0] heptane-4-carboxylate (5a) (3.76 g, 16.39 mmol, 78%) as a colorless oil which was used for the next step without purification.

MS m/z ([M+H-Boc]$^+$) 130.

Step 2: Preparation of intermediate tert-butyl (1S, 3S,6R)-3-[[tert-butyl(dimethyl)silyl] oxymethyl]-7-oxa-4-azabicyclo[4.1.0]heptane-4-carboxylate (5b)

To a solution of tert-butyl (1S,3S,6R)-3-(hydroxymethyl)-7-oxa-4-azabicyclo[4.1.0]heptane-4-carboxylate (5a) (3.90 g, 17.03 mmol) in anhydrous DCM (170 mL) under inert atmosphere at rt was added imidazole (2.90 g, 42.57 mmol) followed by TBDMSCl (3.85 g, 25.55 mmol). The mixture was stirred for 2 h at 20° C. and then the solution was quenched with saturated NaHCO$_3$ aqueous solution and extracted with DCM. The organic phase was dried over Na$_2$SO$_4$, filtered and evaporated. The product was purified by flash chromatography on silica gel (cyclohexane/EtOAc: gradient 90/10 to 50/50) to afford tert-butyl (1S,3S,6R)-3-[[tert-butyl(dimethyl)silyl]oxymethyl]-7-oxa-4-azabicyclo[4.1.0]heptane-4-carboxylate (5b) (3.79 g, 11.03 mmol, 64%) as a colorless oil.

MS m/z ([M+H-Boc]$^+$) 244.

$^1$H NMR (400 MHz, CDCl$_3$): δ (ppm): 0.04 and 0.05 (s, 6H), 0.88 (s, 9H), 1.45 (s, 9H), 2.01 (ddd, J=15.5/7.1/1.7 Hz, 1H), 2.25 (d, J=15.4 Hz, 1H), 3.22-3.31 (m, 2H), 3.40-3.58 (m, 1H), 3.61 (dd, J=9.7/7.7 Hz, 1H), 3.71 (t, J=8.6 Hz, 1H), 3.95-4.30 (m, 2H)

Step 3: Preparation of intermediate tert-butyl (2S,4S,5S)-5-(allyloxyamino)-2-[[tert-butyl(dimethyl)silyl]oxymethyl]-4-hydroxy-piperidine-1-carboxylate (5c)

To a solution of tert-butyl (1S,3S,6R)-3-[[tert-butyl(dimethyl)silyl]oxymethyl]-7-oxa-4-azabicyclo[4.1.0]heptane-4-carboxylate (5b) (4.35 g, 12.69 mmol) in anhydrous MeOH (25.4 mL) under inert atmosphere was added O-allylhydroxylamine (5.45 g, 63.45 mmol). The reactor was sealed and the reaction was stirred 3 days at 80° C. MeOH was evaporated and the residue was purified by flash chromatography on silica gel (Cyclohexane/EtOAc: gradient 90/10 to 0/100) to provide tert-butyl (2S,4S,5S)-5-(allyloxyamino)-2-[[tert-butyl(dimethyl)silyl]oxymethyl]-4-hydroxy-piperidine-1-carboxylate (5c) (3.47 g, 8.32 mmol, 65%) as a colorless oil and starting material (5b) (1.05 g, 3.06 mmol).

MS m/z ([M+H]$^+$) 417.

$^1$H NMR (300 MHz, CDCl$_3$): δ (ppm) 0.09 (s, 6H), 0.91 (s, 9H), 1.46 (s, 9H), 1.76 (dt, J=14.6/4.1 Hz, 1H), 2.17 (ddd, J=14.6/8.0/4.0 Hz, 1H), 3.11 (s, 1H), 3.36 (dd, J=14.3/3.4 Hz, 1H), 3.60 (dd, J=10.5/2.6 Hz, 1H), 3.70-3.83 (m, 1H), 3.90-4.06 (m, 2H), 4.06-4.21 (m, 3H), 4.31 (s, 1H), 5.12-5.30 (m, 2H), 5.50 (s, 1H), 5.82-6.02 (m, 1H)

Step 4: Preparation of intermediate tert-butyl (2S,4S,5S)-5-(allyloxyamino)-4-[tert-butyl(dimethyl)silyl]oxy-2-[[tert-butyl(dimethyl)silyl]oxymethyl]piperidine-1-carboxylate (5d)

To a solution of tert-butyl (2S,4S,5S)-5-(allyloxyamino)-2-[[tert-butyl(dimethyl)silyl]oxymethyl]-4-hydroxy-piperidine-1-carboxylate (5c) (2.63 g, 6.32 mmol) in anhydrous DCM (25 mL) under inert atmosphere at 0° C. was added 2,6-lutidine (0.883 mL, 7.58 mmol) followed by TBDMSOTf (1.52 mL, 6.64 mmol). The mixture was stirred for 2 h at 20° C. and then the solution was extracted with DCM, washed with saturated sodium hydrogencarbonate aqueous solution. The organic phase was dried over Na$_2$SO$_4$, filtered and evaporated. The product was purified by flash chromatography on silica gel (cyclohexane/EtOAc: gradient 99/1 to 90/10) to afford tert-butyl (2S,4S,5S)-5-(allyloxyamino)-4-[tert-butyl(dimethyl)silyl]oxy-2-[tert-butyl(dimethyl)silyl]oxymethyl]piperidine-1-carboxylate (5d) (2.92 g, 5.50 mmol, 87%) as a colorless oil.

MS m/z ([M+H]$^+$) 531.

$^1$H NMR (300 MHz, CDCl$_3$): δ (ppm) 0.01 and 0.02 (s, 6H), 0.06 (s, 6H), 0.87 (s, 9H), 0.89 (s, 9H), 1.43 (s, 9H), 1.59-1.71 (m, 1H), 1.78-1.89 (ddd, J=14.3/6.7/3.4 Hz 1H), 2.89-2.98 (m, 1H), 3.24 (dd, J=14.2/3.1 Hz, 1H), 3.69 (dd, J=10.2/6.4 Hz, 1H), 3.83-4.04 (m, 3H), 4.07-4.24 (m, 2H), 5.13-5.20 (m, 1H), 5.21-5.30 (m, 1H), 5.52 (d, J=6.9 Hz, 1H), 5.91 (ddt, J=17.3/10.3/5.9 Hz, 1H).

Step 5: Preparation of intermediate (3S,4S,6S)-N-allyloxy-4-[tert-butyl(dimethyl)silyl]oxy-6-[[tert-butyl(dimethyl)silyl]oxymethyl]piperidin-3-amine (5e)

To a solution of tert-butyl (2S,4S,5S)-5-(allyloxyamino)-4-[tert-butyl(dimethyl)silyl]oxy-2-[[tert-butyl(dimethyl)silyl]oxymethyl]piperidine-1-carboxylate (5d) (2.92 g, 5.51 mmol) in anhydrous DCM (110 mL) under inert atmosphere at rt, was added slowly TMSI (1.24 mL, 8.26 mmol). The reaction mixture was stirred for 2 h30 at rt. The mixture was then quenched at 0° C. with MeOH (10 mL). The mixture was quenched with Na$_2$S$_2$O$_3$ 15% (200 mL) and extracted with DCM (3×50 mL). The organic phase was dried over Na$_2$SO$_4$, filtered and evaporated and the resulting residue was purified by flash chromatography on silica gel (Cyclohexane/EtOAc: 90/10 to 0/100) to provide (3S,4S,6S)-N-allyloxy-4-[tert-butyl(dimethyl)silyl]oxy-6-[[tert-butyl(dimethyl)silyl]oxymethyl]piperidin-3-amine (5e) (1.88 g, 4.36 mmol, 79%) as a yellow solid.

MS m/z ([M+H]$^+$) 431.

$^1$H NMR (400 MHz, CDCl$_3$): δ (ppm) 0.08 and 0.11 (s, 6H), 0.15 (s, 6H), 0.89 (s, 9H), 0.92 (s, 9H), 1.84 (q, J=12.1 Hz, 1H), 1.98-2.08 (m, 1H), 3.00 (t, J=11.9 Hz, 1H), 3.10-3.20 (m, 1H), 3.28-3.40 (m, 1H), 3.77 (dd, J=12.5/4.1 Hz, 1H), 3.84-4.05 (m, 3H), 4.09-4.17 (m, 2H), 5.16-5.23 (m, 1H), 5.23-5.32 (m, 1H), 5.87 (ddt, J=17.3/10.3/5.9 Hz, 1H), 6.11 (bs, 1H)

Step 6: Preparation of intermediate (2S,4S,5S)-6-allyloxy-4-[tert-butyl(dimethyl)silyl]oxy-2-[[tert-butyl(dimethyl)silyl]oxymethyl]-1,6-diazabicyclo[3.2.1]octan-7-one (5f)

To a solution of (3S,4S,6S)-N-allyloxy-4-[tert-butyl(dimethyl)silyl]oxy-6-[[tert-butyl(dimethyl)silyl]oxymethyl]piperidin-3-amine (5e) (1.88 g, 4.37 mmol) and TEA (2.43 mL, 17.48 mmol) in anhydrous ACN (360 mL) at 0° C. was added diphosgene (0.290 mL, 2.40 mmol) as a solution in acetonitrile (6 mL, flow=0.15 mL/min). Once addition was completed, the reaction was stirred to rt for 1 h. The mixture was washed with water (500 mL), extracted with EtOAc (3×200 mL) dried over Na$_2$SO$_4$, filtered and concentrated. The crude residue was purified by flash chromatography on silica gel (cyclohexane/EtOAc: gradient 100/0 to 0/100) to provide intermediate (2S,4S,5S)-6-allyloxy-4-[tert-butyl(dimethyl)silyl]oxy-2-[[tert-butyl(dimethyl)silyl]oxymethyl]-1,6-diazabicyclo[3.2.1]octan-7-one (5f) (1.22 g, 2.67 mmol, 61%) as a brown oil.

MS m/z ([M+H]$^+$) 457.

$^1$H NMR (400 MHz, CDCl$_3$): δ (ppm) 0.02-0.12 (m, 12H), 0.88 and 0.89 (s, 18H), 1.73 (dt, J=15.4/3.7 Hz, 1H), 2.06 (ddd, J=15.4/7.6/5.4 Hz, 1H), 2.91 (dd, J=11.6/3.3 Hz, 1H), 3.30-3.52 (m, 3H), 3.83 (dd, J=6.5/1.9 Hz, 2H), 4.19-4.28 (m, 1H), 4.35-4.53 (m, 2H), 5.27-5.41 (m, 2H), 5.94-6.09 (m, 1H).

Step 7: Preparation of intermediate (2S,4S,5S)-6-allyloxy-4-hydroxy-2-(hydroxymethyl)-1,6-diazabicyclo[3.2.1]octan-7-one (5g)

To a solution of (2S,4S,5S)-6-allyloxy-4-[tert-butyl(dimethyl)silyl]oxy-2-[[tert-butyl(dimethyl)silyl]oxymethyl]-1, 6-diazabicyclo[3.2.1]octan-7-one (5f) (1.22 g, 2.67 mmol) in anhydrous ACN (27 mL) under inert atmosphere was added dropwise TEA.3HF (0.436 mL, 2.67 mmol). The reaction mixture was stirred at 70° C. for 6 h. The mixture was concentrated under vacuum. The crude was purified by flash chromatography on silica gel (DCM/propan-2-ol: gradient 100/0 to 0/100) to provide (2S,4S,5S)-6-allyloxy-4-hydroxy-2-(hydroxymethyl)-1,6-diazabicyclo[3.2.1]octan-7-one (5g) (0.505 g, 2.21 mmol, 82%) as a colorless oil.

MS m/z ([M+H]$^+$) 229.

$^1$H NMR (400 MHz, CDCl$_3$): δ (ppm) 1.60 (dt, J=15.9/2.3 Hz, 1H), 2.27 (ddd, J=15.8/8.3/2.3 Hz, 1H), 2.89 (dd, J=12.3/3.7 Hz, 1H), 3.39-3.50 (m, 1H), 3.62-3.70 (m, 2H), 3.76-3.92 (m, 3H), 4.16-4.26 (m, 2H), 4.35-4.50 (m, 2H), 5.27-5.41 (m, 2H), 5.92-6.07 (m, 1H)

Step 8: Preparation of intermediate [(2S,4S,5S)-6-allyloxy-4-hydroxy-7-oxo-1,6-diazabicyclo[3.2.1]octan-2-yl]methyl methanesulfonate (5h)

A solution of (2S,4S,5S)-6-allyloxy-4-hydroxy-2-(hydroxymethyl)-1,6-diazabicyclo[3.2.1]octan-7-one (5g) (0.505 g, 2.21 mmol) in DCM (22 mL) was cooled to 0° C. Pyridine (0.21 mL, 2.65 mmol) and MsCl (0.28 mL, 2.32 mmol) were added and the reaction mixture was stirred at the same temperature for 18 h. After concentrating in vacuo, the crude was purified by flash chromatography on silica gel (DCM/MeOH: 100/0 to 90/10) to give the intermediate [(2S,4S,5S)-6-allyloxy-4-hydroxy-7-oxo-1,6-diazabicyclo[3.2.1]octan-2-yl]methyl methanesulfonate (5h) (0.72 g, 2.21 mmol quantitative yield) as an yellow oil.

MS m/z ([M+H]$^+$) 307.

$^1$H NMR (400 MHz, CDCl$_3$): δ (ppm) 1.62 (dt, J=16/2.9 Hz, 1H), 2.25 (ddd, J=15.9/8.0/5.2 Hz, 1H), 2.97 (dd, J=12.3, 3.5 Hz, 1H), 3.11 (s, 3H), 3.50 (d, J=12.3 Hz, 1H), 3.61-3.74 (m, 2H), 4.30-4.52 (m, 5H), 4.59 (dd, J=11.1/8.3 Hz, 1H), 5.28-5.43 (m, 2H), 5.93-6.08 (m, 1H).

Step 9: Preparation of intermediate tert-butyl N-[[(2S,4S,5S)-6-allyloxy-4-hydroxy-7-oxo-1,6-diazabicyclo[3.2.1]octan-2-yl]methyl]carbamate (5i)

The intermediate [(2S,4S,5S)-6-allyloxy-4-hydroxy-7-oxo-1,6-diazabicyclo[3.2.1]octan-2-yl]methyl methanesulfonate (5h) (0.596 g, 1.95 mmol) was dissolved in DMF (7.8 mL) and NaN$_3$ (0.63 g, 9.74 mmol) was added. The reaction mixture was heated at 75° C. overnight and then, concentrated in vacuo. The reaction mixture was quenched with water and extracted with EtOAc. The organic layer was washed with brine, dried over Na$_2$SO$_4$, filtered and concentrated in vacuo. The crude was dissolved in a mixture of THF and toluene (5 mL/5 mL) and PMe3 (1M in THF) (2.92 mL, 2.92 mmol) was added at 0° C. After 30 min stirring at rt, the mixture was cooled to 0° C. and a solution of BocON (0.72 g, 2.92 mmol) in THF (5 mL) was dropwise added. The mixture was stirred at rt for 1h30 and concentrated in vacuo. The crude was purified by flash chromatography on silica gel (cyclohexane/EtOAc: 100/0 to 0/100) to give tert-butyl N-[[(2S,4S,5S)-6-allyloxy-4-hydroxy-7-oxo-1,6-diazabicyclo[3.2.1]octan-2-yl]methyl]carbamate (5i) (324 mg, 0.99 mmol, 50%) as a colorless oil.

MS m/z ([M+H]$^+$) 328.

$^1$H NMR (400 MHz, CDCl$_3$): δ (ppm) 1.43 (s, 9H), 1.57 (d, J=16.2 Hz, 1H), 2.13-2.25 (m, 1H), 2.87 (dd, J=12.1/3.6 Hz, 1H), 3.27-3.44 (m, 2H), 3.53-3.69 (m, 2H), 3.72 (t, J=3.6 Hz, 1H), 4.32 (bs, 1H), 4.36-4.53 (m, 2H), 5.10 (bs, 1H), 5.27-5.42 (m, 2H), 5.94-6.09 (m, 1H).

Step 10: Preparation of intermediate tert-butyl N-[[(2S,5S)-6-allyloxy-4,7-dioxo-1,6-diazabicyclo[3.2.1]octan-2-yl]methyl]carbamate (5j)

To a solution of intermediate tert-butyl N-[[(2S,4S,5S)-6-allyloxy-4-hydroxy-7-oxo-1,6-diazabicyclo[3.2.1]octan-2-yl]methyl]carbamate (5i) (0.350 g, 1.07 mmol) in anhydrous DCM (21 mL) under inert atmosphere at 0° C. was added the Dess-Martin periodinane reagent (0.680 g, 1.60 mmol). The reaction was stirred for 2h30 at rt then the mixture was washed with a saturated NaHCO$_3$ aqueous solution, a 15% Na$_2$S$_2$O$_3$ solution, water, dried oved Na$_2$SO$_4$, filtered and concentrated under vacuum. The residue was purified by flash chromatography on silica gel (cyclohexane/EtOAc: 100/0 to 0/100) to afford intermediate tert-butyl N-[[(2S,5S)-6-allyloxy-4,7-dioxo-1,6-diazabicyclo[3.2.1]octan-2-yl]methyl]carbamate (5j) (0.300 g, 0.92 mmol, 74%) as a colorless oil.

MS m/z ([M+H]$^+$) 326.

$^1$H NMR (400 MHz, CDCl$_3$): δ (ppm) 1.41 (s, 9H), 2.26-2.37 (m, 1H), 2.90 (dd, J=17.9/9.4 Hz, 1H), 3.19-3.41 (m, 3H), 3.41-3.51 (m, 1H), 3.84-3.99 (m, 2H), 4.34-4.49 (m, 2H), 4.89-4.97 (m, 1H), 5.26-5.40 (m, 2H), 5.97 (ddt, J=16.9/10.3/6.5 Hz, 1H).

Step 11: Preparation of intermediate tert-butyl N-[[(2S,5S)-6-allyloxy-4-(2-amino-2-oxo-ethoxy)imino-7-oxo-1,6-diazabicyclo[3.2.1]octan-2-yl]methyl]carbamate (5k)

To a solution of tert-butyl N-[[(2S,5S)-6-allyloxy-4,7-dioxo-1,6-diazabicyclo[3.2.1]octan-2-yl]methyl]carbamate (5j) (0.107 g, 0.33 mmol) in anhydrous MeOH (3.3 mL) under inert atmosphere was added successively pyridine (56 µL, 0.69 mmol) and 2-(aminooxy)acetamide.HCl(0.041 g, 0.33 mmol). The reaction mixture was stirred for 30 min at rt, then concentrated under vacuum. The residue was purified by flash chromatography on silica gel (DCM/MeOH: 100/0 to 95/5) to provide intermediate tert-butyl N-[[(2S,5S)-6-allyloxy-4-(2-amino-2-oxo-ethoxy)imino-7-oxo-1,6-diazabicyclo[3.2.1] octan-2-yl]methyl]carbamate (5k) (0.101 g, 0.25 mmol, ratio Z/E: 60/40, 82%).

MS m/z ([M+H]$^+$) 398.

$^1$H NMR (400 MHz, CDCl$_3$): δ (ppm) 1.39 (bs, 9H), 2.24-2.35 (m, 0.6H), 2.54-2.66 (m, 0.4H), 2.69-2.88 (m, 1H), 3.06-3.21 (m, 2H), 3.22-3.51 (m, 2H), 3.54-3.73 (m, 1H), 4.10-4.16 (m, 0.4H), 4.33-4.59 (m, 4H), 4.96-5.20 (m, 1.6H), 5.25-5.41 (m, 2H), 5.88-6.11 (m, 2H), 6.43 (s, 0.6H), 6.68 (s, 0.4H)

Step 12: Preparation of intermediate sodium [(2S, 5S)-4-(2-amino-2-oxo-ethoxy)imino-2-[(tert-butoxycarbonylamino)methyl]-7-oxo-1,6-diazabicyclo[3.2.1]octan-6-yl] sulfate (5l)

To a solution of intermediate tert-butyl N-[[(2S,4Z,5S)-6-allyloxy-4-(2-amino-2-oxo-ethoxy)imino-7-oxo-1,6-diazabicyclo[3.2.1]octan-2-yl]methyl]carbamate (5k) (0.101 g, 0.254 mmol) and glacial AcOH (29 µL, 0.509 mmol) in anhydrous DCM (2.5 mL) was added in one portion Pd(Ph$_3$)$_4$ (0.147 g, 0.127 mmol). After stirring for 1 h at rt, dry pyridine (2.5 mL) and sulfur trioxide pyridine complex (0.202 g, 1.27 mmol) were added to the mixture and the resulting solution was protected from light and stirred overnight at rt until the sulfatation was completed. The reaction mixture was concentrated under vacuum, diluted with DCM and filtered. The filtrate was concentrated and purified by flash chromatography on silica gel (DCM/acetone 100/0 to 0/100) to provide 25 mg of a colorless oil of triphenyl-(propenyl)-phosphonium [(2S,5S)-4-(2-amino-2-oxo-ethoxy)imino-2-[(tert-butoxycarbonylamino)methyl]-7-oxo-1,6-diazabicyclo[3.2.1]octan-6-yl] sulfate.

This oil was solubilized in a minimal volume of a mixture of water and acetone and applied on a Dowex sodium form column (Dowex® 50WX8 hydrogen form stored with an aqueous solution of 2N NaOH and washed until neutral pH with water). The fractions containing the desired compound were combined, frozen and lyophilized to afford compound sodium [(2S,5S)-4-(2-amino-2-oxo-ethoxy)imino-2-[(tert-butoxycarbonylamino)methyl]-7-oxo-1,6-diazabicyclo[3.2.1]octan-6-yl] sulfate(5l) (0.016 g, 0.036 mmol, ratio Z/E: 60/40, 14% over 2 steps) as a white solid.

MS m/z ([M−H]⁻) 436.

¹H NMR (400 MHz, D$_2$O): δ (ppm) 1.43 (s, 9H), 2.49 (dd, J=17.3/5.5 Hz, 0.6H), 2.70-3.01 (m, 1H), 3.13-3.59 (m, 4.4H), 3.68-3.75 (m, 1H), 4.49-4.65 (m, 2.4H), 5.46 (d, J=2.9 Hz, 0.6H)

Step 13: Preparation of 2,2,2-trifluroacetate and sodium [(2S,5S)-4-(2-amino-2-oxo-ethoxy)imino-2-(azaniumylmethyl)-7-oxo-1,6-diazabicyclo[3.2.1]octan-6-yl] sulfate (example 5)

To a suspension of sodium [(2S,5S)-4-(2-amino-2-oxo-ethoxy)imino-2-[(tert-butoxycarbonylamino)methyl]-7-oxo-1,6-diazabicyclo[3.2.1]octan-6-yl] sulfate (5l) (0.0167 g, 0.036 mmol) in anhydrous DCM (1 mL) to 0° C. was added a solution of TFA (0.4 mL) in anhydrous DCM (0.5 mL). The mixture is stirring 30 min to 0° C. and concentrated. The oil obtained was diluted in water (3 mL), frozen and lyophilized to afford 2,2,2-trifluroacetate and sodium [(2S,5S)-4-(2-amino-2-oxo-ethoxy)imino-2-(azaniumylmethyl)-7-oxo-1,6-diazabicyclo[3.2.1]octan-6-yl] sulfate (Example 5) (0.0164 g, 0.034 mmol, ratio Z/E: 40/60, 95%) as an yellow solid.

MS m/z ([M−H]⁻) 336.

¹H NMR (400 MHz, D$_2$O): δ (ppm) 2.56 (dd, J=17.4/7.5 Hz, 0.6H), 2.67 (dd, J=19.7/4.2 Hz, 0.4H), 2.89 (dd, J=17.4/8.0 Hz, 0.6H), 3.15-3.39 (m, 2.4H), 3.46 (dd, J=12.8/2.7 Hz, 1H), 3.58 (dd, J=12.9/3.1 Hz, 0.6H), 3.65 (dd, J=12.7/3.5 Hz, 0.4H), 3.86-3.97 (m, 1H), 4.56-4.64 (m, 2.4H), 5.44 (d, J=2.9 Hz, 0.6H)

Example 6

Synthesis of 2,2,2-trifluroacetate and sodium [(2S,5S)-4-(2-amino-2-oxo-ethoxy)imino-2-(azaniumylmethyl)-7-oxo-1,6-diazabicyclo[3.2.1]octan-6-yl] sulfate

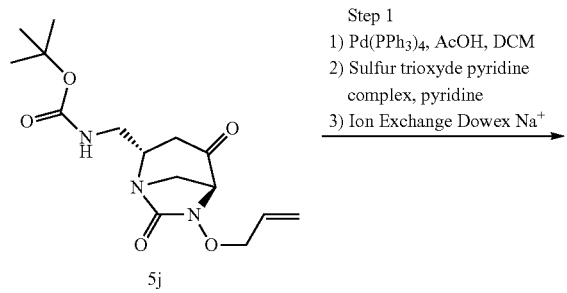

Step 1
1) Pd(PPh$_3$)$_4$, AcOH, DCM
2) Sulfur trioxyde pyridine complex, pyridine
3) Ion Exchange Dowex Na⁺

5j

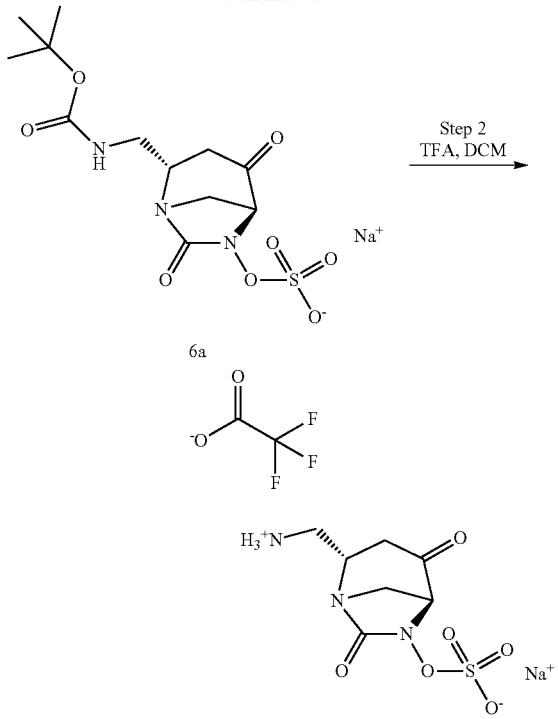

6a

Example 6

Step 1: Preparation of intermediate sodium [(2S,5S)-2-[(tert-butoxycarbonylamino)methyl]-4,7-dioxo-1,6-diazabicyclo[3.2.1]octan-6-yl] sulfate (6a)

To a solution of compound tert-butyl N-[[(2S,5S)-6-allyloxy-4,7-dioxo-1,6-diazabicyclo[3.2.1]octan-2-yl]methyl] carbamate (5j) (0.080 g, 0.246 mmol) and glacial AcOH (28 µL, 0.492 mmol) in anhydrous DCM (2.5 mL) was added in one portion Pd(Ph$_3$)$_4$ (0.142 g, 0.12 mmol). After stirring for 2 h at rt, dry pyridine (2.5 mL) and sulfur trioxide pyridine complex (0.196 g, 1.23 mmol) were added to the mixture and the resulting solution was protected from light and stirred overnight at rt until the sulfatation was completed. The reaction mixture was concentrated under vacuum, diluted with DCM and filtered. The filtrate was concentrated and purified on silica gel (DCM/acetone 100/0 to 0/100) to provide 14.8 mg of a yellow oil of triphenyl-(propenyl)-phosphonium [(2S,5S)-2-[(tert-butoxycarbonylamino)methyl]-4,7-dioxo-1,6-diazabicyclo[3.2.1]octan-6-yl] sulfate.

This oil was solubilized in a minimal volume of a mixture of water and acetone and applied on a Dowex sodium form column (Dowex® 50WX8 hydrogen form stored with an aqueous solution of 2N NaOH and washed until neutral pH with water). The fractions containing the desired compound were combined, frozen and lyophilized to afford compound sodium [(2S,5S)-2-[(tert-butoxycarbonylamino)methyl]-4,7-dioxo-1,6-diazabicyclo[3.2.1]octan-6-yl] sulfate (6a) (0.0095 g, 0.024 mmol, 10% over 2 steps) as an orange solid.

MS m/z ([M−H]⁻) 364.

¹H NMR (400 MHz, D$_2$O, under hydrate and ketone form): δ (ppm) 1.41 (s, 9H), 1.88 (t, J=7.8 Hz, 1H), 2.04 (dd, J=15.7/7.8 Hz, 0.6H), 2.52 (d, J=18.6 Hz, 0.4H), 2.96 (dd, J=18.6/9.2 Hz, 0.3H), 3.20-3.77 (m, 4.4H), 3.82-3.94 (m, 0.3H), 4.11 (d, J=3.8 Hz, 0.7H), 4.35 (d, J=3.5 Hz, 0.3H)

Step 2: Preparation of 2,2,2-trifluroacetate and sodium [(2S,5S)-2-(azaniumylmethyl)-4,7-dioxo-1,6-diazabicyclo[3.2.1]octan-6-yl] sulfate (example 6)

Using the procedure described in example 5 (step 13), sodium [(2S,5S)-2-[(tert-butoxycarbonylamino)methyl]-4,7-dioxo-1,6-diazabicyclo[3.2.1]octan-6-yl] sulfate (6a) (0.0095 g, 0.245 mmol) is converted into 2,2,2-trifluroacetate and sodium [(2S,5S)-2-(azaniumylmethyl)-4,7-dioxo-1,6-diazabicyclo[3.2.1]octan-6-yl] sulfate (example 6) (0.010 g, 0.024 mmol, quantitative yield) as an orange oil.
MS m/z ([M−H]$^-$) 264.

$^1$H NMR (400 MHz, D$_2$O): δ (ppm): 1.89 (d, J=15.6 Hz, 1H), 2.11-2.27 (m, 1H), 2.52-2.63 (m, 0.3H), 2.97-3.81 (m, 4.7H), 4.13 (d, J=3.8 Hz, 0.7H), 4.35 (d, J=3.5 Hz, 0.3H).

$^1$H NMR (400 MHz, DMSO): δ (ppm) 2.33-2.43 (m, 1H), 2.83 (dd, J=18.5/9.5 Hz, 1H), 2.98-3.13 (m, 1H), 3.18-3.31 (m, 1H), 3.36-3.66 (m, 2H), 3.82-3.95 (m, 1H), 4.16 (d, J=3.7 Hz, 1H), 7.81-8.09 (m, 3H)

$^{19}$F NMR (300 MHz, DMSO): δ (ppm): −73 (s, 3F)

Example 7

Biological Activity

Method 1: β-lactamase Inhibitory Activity, Determination of IC$_{50}$ (Table 1)

Enzyme activity was monitored by spectrophotometric measurement of nitrocefin (NCF—TOKU-E, N005) hydrolysis at 485 nm, at room temperature and in assay buffer A: 100 mM Phosphate pH7, 2% glycerol and 0.1 mg/mL Bovine serum albumin (Sigma, B4287). Enzymes were cloned in E. coli expression vector, expressed and purified in house using classical procedures. To a transparent polystyrene plate (Corning, 3628) were added in each well 5 µL DMSO or inhibitor dilutions in DMSO and 80 µL enzyme in buffer A. Plates were immediately read at 485 nm in a microplate spectrophotometer (BioTek, PowerWave HT) to enable background subtraction. After 30 min of pre-incubation at room temperature, 15 µL of NCF (200 µM final) were finally added in each well. Final enzyme concentrations were 0.1 nM (TEM-1), 0.075 nM (SHV-1), 0.4 nM (CTX-M-15), 1 nM (KPC-2), 0.2 nM (P99 AmpC), 0.2 nM (CMY-37), 0.4 nM (AmpC P. aeruginosa), 0.2 nM (OXA-1), 1.2 nM (OXA-11), 0.4 nM (OXA-15) and 0.3 nM (OXA-48). After 20 min incubation at room temperature, plates were once again read at 485 nm. Enzyme activity was obtained by subtracting the final signal by the background, and was converted to enzyme inhibition using non inhibited wells. IC$_{50}$ curves were fitted to a classical Langmuir equilibrium model with Hill slope using XLFIT (IDBS).

Method 2: MIC of Compounds and Synergy with Ceftazidime Against Bacterial Isolates (Table 2 and 3)

Compounds of the present invention were assessed against genotyped bacterial strains alone or in combination with the β-lactam ceftazidime (CAZ). In the assays, MICs of said compounds, or of ceftazidime at fixed concentrations of said compounds were determined by the broth microdilution method according to the Clinical Laboratory Standards Institute (CLSI—M7-A7). Briefly, compounds alone according to the invention were prepared in DMSO and spotted (2 µL each) on sterile polystyrene plates (Corning, 3788). Compounds and ceftazidime dilutions were prepared in DMSO and spotted (1 µL each) on sterile polystyrene plates (Corning, 3788). Log phase bacterial suspensions were adjusted to a final density of 5×10$^5$ cfu/mL in cation-adjusted Mueller-Hinton broth (Becton-Dickinson) and added to each well (98 µL). Microplates were incubated for 16-20 h at 35° C. in ambient air. The MIC of of the compounds was defined as the lowest concentration of said compounds that prevented bacterial growth as read by visual inspection. The MIC of ceftazidime at each compound concentration was defined as the lowest concentration of ceftazidime that prevented bacterial growth as read by visual inspection.

TABLE 2

Bacterial species used in MIC determination

| Strains | | Resistance mechanism |
|---|---|---|
| E. cloacae | 260508 | TEM-1, CTX-M-15 |
| E. coli | UFR61O | TEM-1, KPC-2 |
| K. pneumoniae | BAA-1898 | TEM-1, SHV-11, SHV-12, KPC-2 |
| K. pneumoniae | 160143 | TEM-1, SHV-1, CTX-M-15, KPC-2, OXA-1 |
| K. pneumoniae | UFR68 | TEM-1, SHV-11, CTX-M-15, KPC-3 |
| E. cloacae | P99 | AmpC |
| E. cloacae | UFR85 | TEM-1, CTX-M-15, derepressed AmpC |
| E. cloacae | UFR70 | TEM-1, CTX-M-15, CMY-2, OXA-1, Porin loss |
| K. pneumoniae | UFR77 | CMY-2 |
| E. coli | UFR74 | SHV-1, DHA-1 |
| E. coli | UFR18 | CTX-M-15, OXA-204 |
| E. coli | 131119 | TEM-1, OXA-48 |
| K. oxytoca | UFR21 | TEM-1, CTX-M-15, OXA-48 |
| K. pneumoniae | UFR24 | TEM-1, SHV-2, SHV-11, OXA-1, OXA-48, OXA-47 |
| K. pneumoniae | 6299 | TEM-1, SHV-11, OXA-163 |
| E. coli | RGN238 | OXA-1 |
| K. pneumoniae | 200047 | TEM-1, SHV-32, CTX-M-15, OXA-1 |
| E. coli | 190317 | TEM-1, SHV-12, CTX-M-15, OXA-1 |
| E. coli | UFR32 | TEM-1, VEB-1, OXA-10 |
| E. cloacae | UFR38 | CTX-M-15, NDM-1 |
| C. murliniae | 210102 | VIM-4 |

TABLE 1

IC$_{50}$ (µM) for β-lactamase Inhibitory Activity

| | IC$_{50}$ β-lactamase (µM) | | | | | | | | | | |
|---|---|---|---|---|---|---|---|---|---|---|---|
| | (A) | | | | (C) | | | (D) | | | |
| | TEM-1 | SHV-1 | CTX-M-15 | KPC-2 | AmpC (P99) | CMY-37 | AmpC (PAE) | OXA-1 | OXA-11 | OXA-15 | OXA-48 |
| Example 1 | 0.0032 | 0.0013 | 0.0054 | 0.0078 | 0.0041 | 0.0099 | 0.037 | 0.080 | 0.0041 | 0.00065 | 0.00051 |
| Example 2 | 0.0017 | 0.00074 | 0.00076 | 0.0039 | 0.0032 | 0.017 | 0.11 | 0.0061 | 0.0068 | 0.00084 | 0.0035 |
| Example 3 | 0.0030 | 0.0046 | 0.0020 | 0.033 | 0.0074 | 0.025 | 0.22 | 0.017 | 0.048 | 0.0016 | 0.0057 |
| Example 4 | 0.014 | 0.020 | 0.0030 | 0.068 | 0.035 | 0.012 | 0.40 | 0.061 | 0.16 | 0.0073 | 0.027 |
| Example 5 | 0.11 | 0.064 | 0.13 | 1.8 | 11 | 12 | 12 | 0.37 | 0.43 | 0.0080 | 0.18 |
| Example 6 | 0.28 | 0.34 | 0.51 | 5.1 | 6.4 | 6.8 | 38 | 1.2 | 1.6 | 0.068 | 0.84 |

TABLE 2-continued

Bacterial species used in MIC determination

| | Strains | Resistance mechanism |
|---|---|---|
| E. coli | UFR52 | TEM-1, SHV-12, IMP-8 |
| P. aeruginosa | CIP107051 | TEM-24 |
| P. aeruginosa | CIP105250 | OXA-15 |
| P. aeruginosa | UFR35 | OXA-23 |
| P. aeruginosa | UFR90 | derepressed AmpC, OprD− |
| P. aeruginosa | UFR92 | derepressed AmpC, OprD− |
| P. aeruginosa | UFR93 | derepressed AmpC, OprD−, MexAB+, MexXY+ |
| P. aeruginosa | UFR47 | VIM-1 |
| P. aeruginosa | UFR48 | VIM-2 |
| P. aeruginosa | UFR59 | IMP-29 |

TABLE 3

MIC of compounds

MIC compounds of the invention alone (μg/mL)

| Strains | Example 1 | Example 2 | Example 3 | Example 4 | Example 5 | Example 6 |
|---|---|---|---|---|---|---|
| 260508 | | | | 16 | 32 | >32 |
| UFR61O | | | | >32 | 0.5 | 4 |
| BAA-1898 | >32 | >32 | >32 | >32 | >32 | >32 |
| 160143 | | | | >32 | >32 | >32 |
| UFR68 | | | | >32 | >32 | >32 |
| P99 | >32 | >32 | >32 | 16 | 0.063 | 1 |
| UFR85 | | | | >32 | >32 | >32 |
| UFR70 | | | | >32 | >32 | >32 |
| UFR77 | | | | >32 | >32 | >32 |
| UFR74 | | | | >32 | >32 | >32 |
| UFR18 | | | | 4 | 0.25 | 1 |
| 131119 | >32 | 8 | >32 | >32 | >32 | 2 |
| UFR21 | | | | >32 | >32 | >32 |
| UFR24 | | | | >32 | >32 | >32 |
| 6299 | >32 | >32 | >32 | >32 | >32 | >32 |
| RGN238 | >32 | >32 | >32 | >32 | >32 | >32 |
| 200047 | | | | >32 | >32 | >32 |
| 190317 | >32 | 4 | >32 | 4 | 0.25 | 1 |
| UFR32 | | | | 4 | 1 | 1 |
| UFR38 | | | | 2 | 0.125 | 0.5 |
| 210102 | | | | >32 | >32 | >32 |
| UFR52 | | | | 8 | 8 | 2 |
| CIP107051 | >32 | >32 | >32 | 32 | 4 | 8 |
| CIP105250 | >32 | >32 | >32 | >32 | 32 | 16 |
| UFR35 | | | | | 1 | 4 |
| UFR90 | | | | | 1 | 4 |
| UFR92 | | | | | 2 | 4 |
| UFR93 | | | | | 4 | 8 |
| UFR47 | | | | | 2 | 4 |
| UFR48 | | | | | 2 | 8 |
| UFR59 | | | | | 4 | 16 |

TABLE 4

MIC of Ceftazidime/compound combinations combination of CAZ and compounds of the invention at 4 μg/mL: MIC(μg/mL)

| Strains | CAZ | Example 1 | Example 2 | Example 3 | Example 4 | Example 5 | Example 6 |
|---|---|---|---|---|---|---|---|
| 260508 | 128 | | 1 | | | <0.25 | ≤0.25 |
| UFR61O | 128 | | 0.5 | | | <0.25 | 1 |
| BAA-1898 | 256 | 128 | 64 | 64 | ≤0.125 | 0.5 | 1 |
| 160143 | 128 | | 8 | | | 0.5 | 2 |
| UFR68 | >128 | | 64 | | | 1 | 1 |
| P99 | 128 | 64 | 4 | 32 | 0.25 | <0.25 | <0.25 |
| UFR85 | 128 | | 1 | | | ≤0.25 | ≤0.25 |
| UFR70 | >128 | | 8 | | | 1 | 2 |
| UFR77 | 64 | | 32 | | | 2 | 2 |
| UFR74 | 64 | | 0.5 | | | 1 | 0.5 |
| UFR18 | >128 | | 1 | | | <0.25 | ≤0.25 |
| 131119 | 0.5 | | ≤0.25 | | | <0.25 | ≤0.25 |
| UFR21 | 128 | | 2 | | | ≤0.25 | ≤0.25 |
| UFR24 | >128 | | 2 | | | 1 | 4 |
| 6299 | 256 | 32 | 2 | 4 | 0.25 | 0.25 | 2 |
| RGN238 | 0.5 | | ≤0.25 | | | ≤0.25 | ≤0.25 |
| 200047 | 128 | | 0.5 | | | ≤0.25 | 1 |
| 190317 | 128 | 4 | ≤0.125 | ≤0.125 | <0.25 | <0.25 | <0.25 |
| UFR32 | >128 | | 0.5 | | | ≤0.25 | ≤0.25 |
| UFR38 | >128 | | | | | ≤0.25 | <0.25 |
| 210102 | >128 | | | | | 1 | 4 |
| UFR52 | >128 | | | | | ≤0.25 | <0.25 |
| CIP107051 | 256 | 64 | 16 | 32 | 8 | <0.25 | 0.125 |
| CIP105250 | 256 | 64 | 64 | 32 | 8 | ≤0.25 | 2 |
| UFR35 | 2 | | | | | <0.25 | <0.25 |
| UFR90 | 64 | | | | | <0.25 | <0.25 |
| UFR92 | 32 | | | | | <0.25 | <0.25 |
| UFR93 | >128 | | | | | <0.25 | 0.5 |
| UFR47 | >128 | | | | | <0.25 | ≤0.25 |
| UFR48 | 256 | | | | | <0.25 | ≤0.25 |
| UFR59 | 128 | | | | | <0.25 | ≤0.25 |

The invention claimed is:
1. A compound of formula (I)

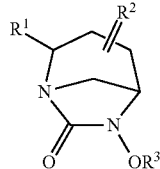

wherein:
R$^1$ is selected from the group consisting of a carbon-linked 4- or 5- or 6-member heterocycle comprising at least one nitrogen atom that is aromatic or saturated or totally unsaturated or partially unsaturated and optionally substituted by one or more T$^1$, —CN, —C(O)NHQ$^1$, —C(O)NHOQ$^1$, —C(O)NH—NHQ$^1$, —C(O)O—NHQ$^1$, —C(O)OQ$^1$, —(CH$_2$)$_m$OC(O)OQ$^1$, —(CH$_2$)$_m$OQ$^1$, —(CH$_2$)$_m$OC(O)Q$^1$, —(CH$_2$)$_m$OC(O)NQ$^1$Q$^2$, —(CH$_2$)$_m$—NHC(O)Q$^1$, —(CH$_2$)$_m$NHS(O)$_2$Q$^1$, —(CH$_2$)$_m$NHS(O)$_2$NQ$^1$Q$^2$, —(CH$_2$)$_m$NHC(O)OQ$^1$, —(CH$_2$)$_m$NHC(O)NQ$^1$Q$^2$, —(CH$_2$)$_m$NHQ$^3$, —(CH$_2$)$_m$NH—C(NHQ$^3$)=NQ$^4$, —(CH$_2$)$_m$NH—CH=NQ$^3$, and —C(NHQ$^3$)=NQ$^4$;

R$^2$ is O or NOQ$^5$;
R$^3$ is SO$_3$H, CFHCO$_2$H or CF$_2$CO$_2$H;
Q$^1$ and Q$^2$ are one of the following:
  Q$^1$ and Q$^2$, identical or different, are independently selected from the group consisting of H, —(CH$_2$)$_p$NHQ$^3$, —(CH$_2$)$_p$—NH—C(NHQ$^3$)=NQ$^4$, (CH$_2$)$_p$—NH—CH=NQ$^3$, (CH$_2$)$_q$—C(NHQ$^3$)=NQ$^4$, —(CH$_2$)$_p$OQ$^3$, and —(CH$_2$)$_q$CONHQ$^3$; or
  Q$^1$ and Q$^2$, identical or different, are independently selected from the group consisting of C$_1$-C$_3$ alkyl that is optionally substituted by one or more T$^2$, and —(CH$_2$)$_n$—(4- or 5- or 6-member heterocycle) that is optionally substituted by one or more T$^2$; or
  Q$^1$ and Q$^2$ and the nitrogen atom to which they are bonded form together a saturated or partially unsaturated 4- or 5- or 6-member heterocycle comprising 1 or 2 or 3 heteroatoms;
Q$^3$ and Q$^4$, identical or different, are independently selected from the group consisting of H and C$_1$-C$_3$ alkyl;
Q$^5$ is one of the following:
  Q$^5$ is selected from the group consisting of C$_1$-C$_3$ alkyl that is optionally substituted by one or more T$^3$, C$_1$-C$_3$ fluoroalkyl; —(CH$_2$)$_n$—C$_3$-C$_6$ cycloalkyl that is optionally substituted by one or more T$^3$; —(CH$_2$)$_n$—C$_3$-C$_6$ cyclofluoroalkyl that is optionally substituted by one or more T$^3$, and —(CH$_2$)$_n$—(4- or 5- or 6-member heterocycle) that is optionally substituted by one or more T$^3$; or
  Q$^5$ is selected from the group consisting of H, (CH$_2$)$_p$OQ$^6$, —(CH$_2$)$_q$—CN, —(CH$_2$)$_p$OC(O)Q$^6$, —(CH$_2$)$_q$—C(O)OQ$^6$, —(CH$_2$)$_p$—OC(O)OQ$^6$, —(CH$_2$)$_p$—OC(O)NQ$^6$Q$^7$, —(CH$_2$)$_q$—C(O)NQ$^6$Q$^7$, —(CH$_2$)$_q$—C(O)NQ$^6$OQ$^7$, —(CH$_2$)$_q$—C(O)NQ$^6$—NQ$^6$Q$^7$, —(CH$_2$)$_p$—NQ$^6$C(O)Q$^7$, —(CH$_2$)$_p$NQ$^6$S(O)$_2$Q$^7$, —(CH2)$_p$NQ$^6$S(O)$_2$NQ$^6$Q$^7$, —(CH$_2$)$_p$—NQ$^6$C(O)OQ$^6$, —(CH$_2$)$_p$—NQ$^6$C(O)NQ$^6$Q$^7$, —(CH$_2$)$_p$NQ$^6$Q$^7$, —(CH$_2$)$_p$—NH—C(NHQ$^3$)=NQ$^4$, —(CH$_2$)$_p$—NH—CH=NQ$^3$, and (CH$_2$)$_q$C(NHQ$^3$)=NQ$^4$;

T$^1$ is one of the following:
  T$^1$, identical or different, is independently selected from the group consisting of F, —(CH$_2$)$_n$OQ$^1$, —(CH$_2$)$_n$—CN, —(CH$_2$)$_n$OC(O)Q$^1$, —(CH$_2$)$_n$—C(O)OQ$^1$, —(CH$_2$)$_n$—OC(O)OQ$^1$, —(CH$_2$)$_n$—OC(O)NHQ$^1$, —(CH$_2$)$_n$—C(O)NHQ$^1$, —(CH$_2$)$_n$—C(O)NHOQ$^1$, —(CH$_2$)$_n$—C(O)NH—NHQ$^1$, —(CH$_2$)$_n$—C(O)O—NHQ$^1$, —(CH$_2$)$_n$—NHC(O)Q$^1$, —(CH$_2$)$_n$NHS(O)$_2$Q$^1$, —(CH$_2$)$_n$NHS(O)$_2$NQ$^1$Q$^2$, —(CH$_2$)$_n$—NHC(O)OQ$^1$, —(CH$_2$)$_n$—NHC(O)NQ$^1$Q$^2$, —(CH$_2$)$_n$NHQ$^1$, —(CH$_2$)$_n$—NH—C(NHQ$^3$)=NQ$^4$, —(CH$_2$)$_n$—NH—CH=NQ$^3$, and (CH$_2$)$_n$—C(NHQ$^3$)=NQ$^4$; or
  T$^1$, identical or different, is independently selected from the group consisting of C$_1$-C$_3$ alkyl that is optionally substituted by one or more T$^2$, C$_1$-C$_3$ fluoroalkyl that is optionally substituted by one or more T$^2$, O—C$_1$-C$_3$ fluoroalkyl that is optionally substituted by one or more T$^2$, and —(CH$_2$)$_n$—(4- or 5- or 6-member comprising at least one nitrogen atom that is aromatic or saturated or totally unsaturated or partially unsaturated) that is optionally substituted by one or more T$^2$;

T$^2$, identical or different, is independently selected from the group consisting of OH, NH$_2$, and CONH$_2$;

T$^3$, identical or different, is independently selected from the group consisting of H, F, C$_1$-C$_3$ alkyl, C$_1$-C$_3$ fluoroalkyl, O—C$_1$-C$_3$ fluoroalkyl, —(CH$_2$)$_n$OQ$^6$, —(CH$_2$)$_n$—C$_3$-C$_6$ cycloalkyl, —(CH$_2$)$_n$—C$_3$-C$_6$ cyclofluoroalkyl, —(CH$_2$)$_n$-heterocycle, —(CH$_2$)$_n$—CN, —(CH$_2$)$_n$OC(O)Q$^6$, —(CH$_2$)$_n$—C(O)OQ$^6$, —(CH$_2$)$_n$—OC(O)OQ$^6$, —(CH$_2$)$_n$—OC(O)NQ$^6$Q$^7$, —(CH$_2$)$_n$—C(O)NQ$^6$Q$^7$, —(CH$_2$)$_n$—C(O)NQ$^6$OQ$^7$, —(CH$_2$)$_n$—C(O)NQ$^6$—NQ$^6$Q$^7$, —(CH$_2$)$_n$—C(O)O—NHQ$^6$, —(CH$_2$)$_n$—NQ$^6$C(O)Q$^7$, —(CH$_2$)$_n$NQ$^6$S(O)$_2$Q$^7$, —(CH$_2$)$_n$NQ$^6$S(O)$_2$NQ$^6$Q$^7$, —(CH$_2$)$_n$—NQ$^6$C(O)OQ$^7$, —(CH$_2$)$_n$—NQ$^6$C(O)NQ$^6$Q$^7$, —(CH$_2$)$_n$NQ$^6$Q$^7$, —(CH$_2$)$_n$—NH—C(NHQ$^3$)=NQ$^4$, —(CH$_2$)$_n$—NH—CH=NQ$^3$, and —(CH$_2$)$_n$—C(NHQ$^3$)=NQ$^4$;

Q$^6$ and Q$^7$ are one of the following:
  Q$^6$ and Q$^7$, identical or different, are independently selected from the group consisting of H, C$_1$-C$_3$ alkyl, —(CH$_2$)$_p$NHQ$^3$, —(CH$_2$)$_p$—NH—C(NHQ$^3$)=NQ$^4$, (CH$_2$)$_p$—NH—CH=NQ$^3$, (CH$_2$)$_q$—C(NHQ$^3$)=NQ$^4$, —(CH$_2$)$_p$OQ$^3$, —(CH$_2$)$_q$C(O)NQ$^3$Q$^4$, and —(CH$_2$)$_n$—(4- or 5- or 6-member heterocycle comprising at least one nitrogen atom that is aromatic or saturated or totally unsaturated or partially unsaturated); or
  Q$^6$ and Q$^7$ and the nitrogen atom to which they are bonded form together a saturated or partially unsaturated 4- or 5- or 6-membered heterocycle comprising 1 or 2 or 3 heteroatoms;

m, identical or different, is independently selected from the group consisting of 1 and 2;
n, identical or different, is independently selected from the group consisting of 0, 1, 2, and 3;
p, identical or different, is independently selected from the group consisting 2 and 3;
q, identical or different, is independently selected from the group consisting of 1, 2, and 3;
wherein any carbon atom present within any of the foregoing alkyls, cycloalkyls, fluoroalkyls, cyclofluoroalkyls, and heterocycles can be oxidized to form a C=O group;

wherein any sulphur atom present within any of the foregoing heterocycles can be oxidized to form a S=O group or a $S(O)_2$ group; and wherein any nitrogen atom, within a heterocycle or within a tertiary amino group, can be further quaternized by a methyl group; or a racemate, an enantiomer, a diastereoisomer, a geometric isomer, or a pharmaceutically acceptable salt of formula (I).

2. The compound according to claim 1 of formula (A)

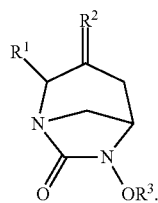

(A)

3. The compound according to claim 1 selected from the group consisting of formulae (A1), (A2), (B1), and (B2)

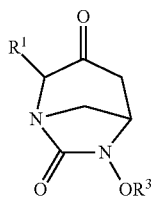

(A1)

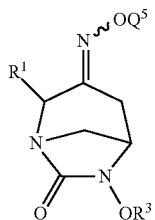

(A2)

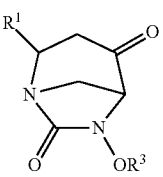

(B1)

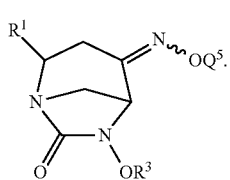

(B2)

4. The compound according to claim 1 of formula (I*)

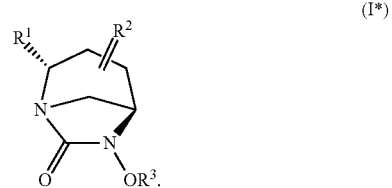

(I*)

5. The compound according to claim 1, wherein $R^1$ is one of the following:

$R^1$ is selected from the group consisting of the carbon-linked 4- or 5- or 6-member heterocycle comprising at least one nitrogen atom that is aromatic or saturated or totally unsaturated or partially unsaturated and optionally substituted by one or more $T^1$, —CN, —C(O)NHQ$^1$, —C(O)NHOQ$^1$, —C(O)NH—NHQ$^1$, —C(O)O—NHQ$^1$, —C(O)OQ$^1$, —(CH$_2$)OC(O)OQ$^1$, —(CH$_2$)$_2$OC(O)OQ$^1$, —(CH$_2$)OQ$^1$, —(CH$_2$)$_2$OQ$^1$, —(CH$_2$)OC(O)Q$^1$, —(CH$_2$)$_2$OC(O)Q$^1$, —(CH$_2$)—OC(O)NQ$^1$Q$^2$, —(CH$_2$)$_2$OC(O)NQ$^1$Q$^2$, —(CH$_2$)NHC(O)Q$^1$, —(CH$_2$)$_2$—NHC(O)Q$^1$, —(CH$_2$)NHS(O)$_2$Q$^1$, —(CH$_2$)$_2$NHS(O)$_2$Q$^1$, —(CH$_2$)NHS(O)$_2$NQ$^1$Q$^2$, —(CH$_2$)$_2$NHS(O)$_2$NQ$^1$Q$^2$, —(CH$_2$)NHC(O)OQ$^1$, —(CH$_2$)$_2$NHC(O)OQ$^1$, —(CH$_2$)NHC(O)NQ$^1$Q$^2$, and —(CH$_2$)$_2$NHC(O)NQ$^1$Q$^2$; or $R^1$ is selected from the group consisting of —(CH$_2$)NHQ$^3$, —(CH$_2$)$_2$NHQ$^3$, —(CH$_2$)NH—C(NHQ$^3$)=NQ$^4$, —(CH$_2$)$_2$NH—C(NHQ$^3$)=NQ$^4$, —(CH$_2$)NH—CH=NQ$^3$, —(CH$_2$)$_2$NH—CH=NQ$^3$, and —C(NHQ$^3$)=NQ$_4$.

6. The compound according to claim 1 wherein $R^1$ is one of the following:

$R^1$ is selected from the group consisting of the carbon-linked 4- or 5- or 6-member heterocycle comprising at least one nitrogen atom that aromatic or saturated or totally unsaturated or partially unsaturated and optionally substituted by one or more $T^1$, —CN, —C(O)NHQ$^1$, —C(O)NHOQ$^1$, —C(O)NH—NHQ$^1$, and —(CH$_2$)$_2$Q$^1$; or $R^1$ is —(CH$_2$)NHQ$^3$ or —(CH$_2$)NH—C(NHQ$^3$)=NQ$^4$.

7. The compound according to claim 1, wherein:

$R^1$ is selected from the group consisting of —C(O)NHQ$^1$, —C(O)NHOQ$^1$, —C(O)NH—NHQ$^1$, —C(O)OQ$^1$, —(CH$_2$)$_m$NHQ$^3$, and —(CH$_2$)$_m$NH—C(NHQ$^3$)=NQ$^4$;

$Q^1$ and $Q^3$ are independently selected from the group consisting of H and $C_1C_3$ alkyl;

$Q^5$ is selected from the group consisting of —(CH$_2$)$_q$—C(O)NQ$^6$Q$^7$; —(CH$_2$)$_q$—C(O)NQ$^6$OQ$^7$; —(CH$_2$)$_q$—C(O)NQ$^6$—NQ$^6$Q$^7$; —(CH$_2$)$_p$NQ$^6$Q$^7$; and —(CH$_2$)$_p$—NH—C(NHQ$^3$)=NQ$^4$; and $Q^4$, $Q^6$, and $Q^7$, identical or different, are independently selected from the group consisting of H and $C_1$-$C_3$alkyl.

8. The compound according to claim 1, wherein:

$R^1$ is selected from the group consisting of —C(O)NHQ$^1$, —C(O)OQ$^1$, and —(CH$_2$)$_m$NHQ$^3$;

$Q^1$ and $Q^3$ are independently selected from the group consisting of H and $C_1$-$C_3$alkyl;

m is 1;

$Q^5$ is selected from the group consisting of —(CH$_2$)$_q$—C(O)NQ$^6$Q$^7$ and —(CH$_2$)$_p$NQ$^6$Q$^7$;

p is 2;

q is 1 or 2; and $Q^4$, $Q^6$, and $Q^7$, identical or different, are independently selected from the group consisting of H and $C_1$-$C_3$alkyl.

9. The compound according to claim 1, wherein $R^3$ is $SO_3H$ or $CF_2COOH$.

10. An intermediate compound for the preparation of the compound according to claim 1, wherein the intermediate compound is selected from the group consisting of

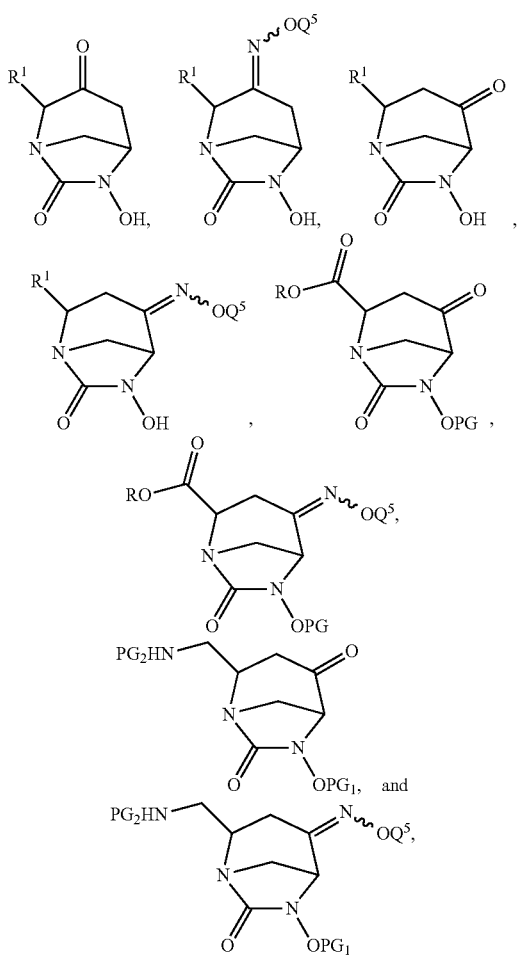

wherein:
R is alkyl or benzyl; and
PG, $PG_1$, and $PG_2$, identical or different, are independently selected protective groups.

11. An intermediate compound for the preparation of the compound according to claim 1, wherein the intermediate compound is selected from the group consisting of

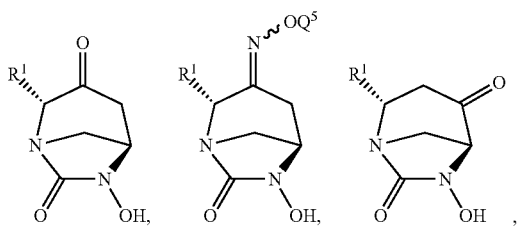

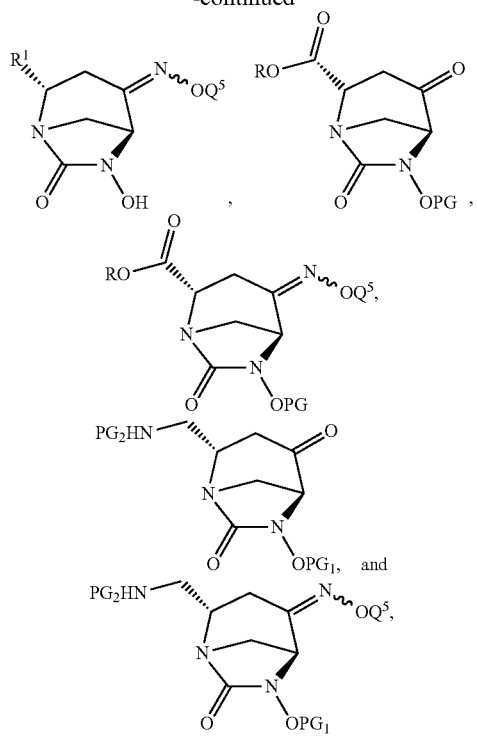

wherein:
R is alkyl or benzyl; and
PG, $PG_1$, and $PG_2$, identical or different, are independently selected protective groups.

12. A pharmaceutical composition comprising the compound of claim 1.

13. The pharmaceutical composition according to claim 12 further comprising an antibacterial compound selected from aminoglycosides, β-lactams, glycylcyclines, tetracyclines, quinolones, fluoroquinolones, glycopeptides, lipopeptides, macrolides, ketolides, lincosamides, streptogramins, oxazolidinones, polymyxins and combinations thereof.

14. The pharmaceutical composition according to claim 13, wherein the β-lactam compound is selected from the group consisting of penicillin, cephalosporins, penems, carbapenems, monobactam, and combinations thereof.

15. The pharmaceutical composition according to claim 12 further comprising a pharmaceutically acceptable excipient.

16. A pharmaceutical composition comprising the compound of claim 2 and ceftazidime.

17. A pharmaceutical composition according comprising the compound of claim 3 and ceftazidime.

18. A pharmaceutical composition according comprising the compound of claim 4 and ceftazidime.

19. A kit comprising two distinct pharmaceutical compositions according to claim 12.

20. The kit according to claim 19 further comprising a third pharmaceutical composition that comprises ceftazimide.

21. A method for the treatment of a bacterial infection in a patient, the method comprising the administering a therapeutically effective amount of the compound of claim 1.

22. The method according to claim 21, wherein the bacterial infection is caused by bacteria producing one or more β-lactamases.

23. The method according to claim 21, wherein the bacterial infection is caused by gram-negative bacteria.
24. The compound according to claim 1 of formula (B)
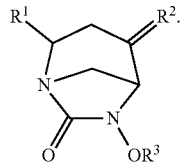
(B)
25. The compound according to claim 1 selected from the group consisting of formula (A*) and formula (B*)
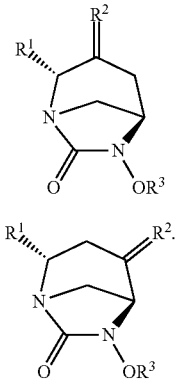
(A*)
(B*)
26. The compound according to claim 1 selected from the group consisting of formula (A1*), formula (A2*), formula (B1*), and formula (B2*)
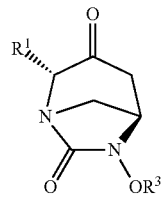
(A1*)
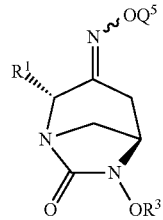
(A2*)
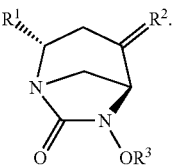
(B1*)
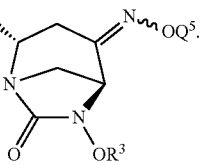
(B2*)
* * * * *